(12) United States Patent
Zimmermann et al.

(10) Patent No.: US 11,781,109 B2
(45) Date of Patent: Oct. 10, 2023

(54) METHODS OF PRODUCING BIOENGINEERED NEURONAL ORGANOIDS (BENOS) AND USES THEREOF

(71) Applicant: Georg-August-Universität Göttingen Stiftung Öffentlichen Rechts Universitätsmedizin, Goettingen (DE)

(72) Inventors: Wolfram-Hubertus Zimmermann, Goettingen (DE); Maria Zafeiriou, Goettingen (DE)

(73) Assignee: GEORGE-AUGUST-UNIVERSITAET GOETTINGEN STIFTUNG OEFFENLICHEN RECHTS, UNIVERSITAETSMEDIZIN, Goettingen (DE)

( * ) Notice: Subject to any disclaimer, the term of this patent is extended or adjusted under 35 U.S.C. 154(b) by 859 days.

(21) Appl. No.: 16/621,707

(22) PCT Filed: Jun. 8, 2018

(86) PCT No.: PCT/EP2018/065204
§ 371 (c)(1),
(2) Date: Dec. 12, 2019

(87) PCT Pub. No.: WO2018/228948
PCT Pub. Date: Dec. 20, 2018

(65) Prior Publication Data
US 2020/0208105 A1 Jul. 2, 2020

(30) Foreign Application Priority Data
Jun. 13, 2017 (EP) .................................... 17175874

(51) Int. Cl.
*C12N 5/0793* (2010.01)
*C12N 5/079* (2010.01)
*G01N 33/50* (2006.01)

(52) U.S. Cl.
CPC ......... *C12N 5/0619* (2013.01); *C12N 5/0622* (2013.01); *G01N 33/5058* (2013.01); *C12N 2500/30* (2013.01); *C12N 2500/90* (2013.01); *C12N 2501/115* (2013.01); *C12N 2501/15* (2013.01); *C12N 2501/42* (2013.01); *C12N 2503/02* (2013.01); *C12N 2506/02* (2013.01); *C12N 2506/45* (2013.01); *C12N 2513/00* (2013.01); *C12N 2533/54* (2013.01)

(58) Field of Classification Search
None
See application file for complete search history.

(56) References Cited

PUBLICATIONS

Zimmermann et al. Tissue Engineering of a Differentiated Cardiac Muscle Construct (2002) Circulation Research, 90, pp. 223-230. (Year: 2002).*

Stipursky et al. TGF-B1 promotes cerebral cortex radial glia-astrocyte differentiation in vivo (2014), Frontiers in Cellular Neuroscience, 393, pp. 1-13. (Year: 2014).*
Kothapalli et al. 3D matrix microenvironment for targeted differentiation of embryonic stem cells into neural and glial lineages (2013) Biomaterials, 34, pp. 5995-6007. (Year: 2013).*
Lancaster et al. Guided self-organization and cortical plate formation in human brain organoids (2017) Nature Biotechnology, 35, pp. 659-666. (Year: 2017).*
Quadrato, Giorgia et al., Nature, 545(7652), pp. 48-53, May 4, 2017.
Chambers SM et al., "Highly efficient neural conversion of human ES and iPS cells by dual inhibition of SMAD signaling". Nat Biotechnol. 2009; 27 (3): 275-280.
Crawford TQ and Roelink H, "The Notch Response Inhibitor DAPT Enhances Neuronal Differentiation in Embryonic Stem Cell-Derived Embryoid Bodies Independently of Sonic Hedgehog Signaling". Dev Dyn. 2007; 236 (3): 886-92.
Feng Y et al., "Rho Kinase (ROCK) Inhibitors and Their Therapeutic Potential". J Med Chem. 2016; 59 (6): 2269-2300.
Jucker M et al., "Fetal Rat Septal Cells Adhere to and Extend Processes on Basement Membrane, Laminin, and a Synthetic Peptide From the Laminin A Chain Sequence". J Neurosci Res. 1991; 28 (4): 507-517.
Kleinman HK et al., "Isolation and Characterization of Type IV Procollagen, Laminin, and Heparan Sulfate Proteoglycan from the EHS Sarcoma". Biochemistry. 1982; 21 (24): 6188-93.
Kriks S et al., "Dopamine neurons derived from human ES cells efficiently engraft in animal models of Parkinson's disease". Nature. 2011; 480 (7378): 547-51.
Lancaster MA et al., "Cerebral organoids model human brain development and microcephaly". Nature. 2013; 501 (7467): 373-9.
Lancaster MA and Knoblich JA, "Organogenesis in a dish: Modeling development and disease using organoid technologies". Science. 2014; 345 (6194): 1247125.
Olsauskas-Kuprys R et al., "Gamma secretase inhibitors of Notch signaling". Onco Targets Ther. 2013; 6: 943-955.
Qian X et al., "Brain Region-specific Organoids using Mini-bioreactors for Modeling ZIKV Exposure". Cell. 2016; 165 (5): 1238-1254.
Stover AE and Schwartz PH, "Adaptation of Human Pluripotent Stem Cells to Feeder-Free Conditions in Chemically Defined Medium with Enzymatic Single-Cell Passaging". Methods Mol Biol. 2011; 767: 137-46.

(Continued)

*Primary Examiner* — Emily A Cordas
*Assistant Examiner* — Maytee Marie Contes de Jesus
(74) *Attorney, Agent, or Firm* — Stacey J. Farmer

(57) ABSTRACT

The present invention relates to the field of in vitro 3D modeling of neural tissues, particularly of the brain. There is the need of developing cell culture models of neural tissue that reflect physiological aspects of neural tissue. The present invention provides methods of producing bioengineered neuronal organoids (BENOs) which form functional neuronal networks. The present invention also relates to uses and applications of the produced BENOs, e.g., in the fields of drug screening and personalized medicine.

10 Claims, 12 Drawing Sheets
(12 of 12 Drawing Sheet(s) Filed in Color)

(56) References Cited

PUBLICATIONS

Kuijlaars, J et al. "Sustained synchronized neuronal network activity in a human astrocyte co-culture system". Scientific Reports. Nov. 7, 2016; 6, 36529; doi 10.1038/srep36529.

Birey et al. "Assembly of functionally integrated human forebrain spheroids". Nature. 2017, vol. 545, pp. 54-78.

Bagley, J, et al. "Fused cerebral organoids model interactions between brain regions". Nature Methods, May 10, 2017; doi:10.1038/nmeth.4304.

Paca, A, et al. "Functional cortical neurons and astrocytes from human pluripotent stem cells in 3D culture". Nat. Methods. Jul. 2015; 12(7):671-678.

Kothapalli, C. "3D matrix microenvironment for targeted differentiation of embryonic stem cells into neural and glial lineages". Biomaterials 34 (2013): 5995-6007.

Tiburcy, M et al. "Defined engineered human myocardium with advanced maturation for applications in heart failure modelling and repair". Circulation. May 9, 2017; 135(19):1832-1847.

\* cited by examiner

METHODS OF PRODUCING BIOENGINEERED NEURONAL ORGANOIDS (BENOS) AND USES THEREOF

CROSS-REFERENCE TO RELATED APPLICATIONS

This application is a national phase entry under 35 U.S.C. § 371 of International Patent Application PCT/EP2018/065204, filed Jun. 8, 2018, published as International Patent Publication WO 2018/28898 on Dec. 20, 2018, which claims the benefit of European Patent Application EP 17175874.1, filed on Jun. 13, 2017, and European Patent Application EP 17205951.1, filed on Dec. 7, 2017, the contents of all are hereby incorporated by reference.

BACKGROUND OF THE INVENTION

In vitro 3D modeling of neural tissues, in particular tissues derived from a mammalian brain, such as a human brain, represents a powerful tissue bioengineering tool permitting the study of complex neuronal cell systems. In general, 3D cell culture systems offer faster cell differentiation, higher cell complexity and longevity compared to the respective 2D culture systems. A promising approach for the in vitro 3D modeling of neural tissues involves the use of pluripotent stem cells (PSCs), which have been employed in the modelling of various human tissues and organs. Such advantages of 3D modeling methodologies in combination with recent technologies used, for example, in the reprogramming of patient fibroblasts into induced PSCs, collectively offer a new horizon for elucidating the underlying molecular mechanisms responsible for a variety of human neuron-based diseases.

Numerous protocols for inducing neural differentiation of human stem cells exist in the literature. One such method involves an induction of the neuroectoderm by dual SMAD (Sma and Mad Related Family) signaling pathway inhibition (i.e., by BMP and TGF beta inhibition) for about 8-12 days in culture (Chambers, Fasano et al., Nat. Biotechnol., 2009). At this time point, the majority of the stem cells transform into neural progenitor cells (NPCs). After day 12, several protocols (Lancaster and Knoblich, Science, 2014) allow spontaneous differentiation of the cells to various neuronal and glial cells, while other protocols (Qian, Nguyen et al., Cell, 2016; Birey, Andersen et al., Nature, 2017) apply various patterning factors to pattern the tissues, or neurotrophic factors (BDNF, GDNF) to enhance neuronal survival. Moreover, it has been observed that dbcAMP addition or notch inhibition by DAPT can enhance neuronal differentiation of such pluripotent cells (Crawford and Roelink, Dev. Dyn., 2007; Kriks, Shim et al., Nature, 2011). Differences in the factors used for neural induction and differentiation as well as the timing of the treatments define the differentiation potential afforded by these procedures. In another report, human cerebral organoids were produced as a model for microcephaly, a disease that is not easily reproducible using mouse models (Lancaster et al., Nature, 2013, Qian, Nguyen et al., Cell, 2016).

Despite the advances in human neuronal organoid generation, there still exist numerous deficiencies limiting the utility of existing neuronal organoids. For example, known methods lack a precise definition of neuronal organoids; such organoids thus commonly display high phenotypic variability. This is partially due to a routine use of Matrigel®, which is a known composition derived from Engelbreth-Holm-Swarm mouse sarcomas and commonly utilized as a neurogenesis supporting substrate.

Another drawback associated with known methods is a lack of neuronal network function of the produced organoids, which thus significantly limits any investigation into neuronal functionality and plasticity. Disease modeling and drug development is also restricted due to the remote phenotypic resemblance of known produced neuronal organoid structures compared to normal brain tissue.

Thus, there is a need for methods for generating neuronal organoids based on a use of chemically defined components in order to allow consistency in the structures produced. Furthermore, there is a need to produce neuronal organoids capable of forming functional neuronal networks in order to meaningfully mimic natural neural structures.

The present invention provides methods permitting both robust and reproducible neural differentiation in a well-defined 3D cell culture system, which further provides a sound basis for investigations into the formation, and plasticity characteristics, of a functional neuronal network.

The organoids of the present invention further offer a valuable tool in drug development. For example, such organoids can meaningfully decrease the typically exorbitant costs associated with both preclinical and clinical drug development, at least because of a decreased need for animal-based experimentation and a reduced number of patients required in clinical trials when predicting post marketing outcome. In addition, novel biologicals (e.g., non-coding RNA therapeutics) and genome editing (e.g., using CRISPR-based platforms) can be tested efficiently in human models. The rapid developments in this field therefore benefit from the availability of highly predictive human organoid models such as those provided by the present invention.

SUMMARY OF THE INVENTION

The present invention relates to a method for producing a bioengineered neuronal organoid (BENO) from pluripotent stem cells (PSCs), the method comprising:
(A) providing a source of PSCs;
(B) culturing the PSCs of step (A), embedded in a matrix immersed in cell culture medium;
(C) culturing the PSCs in said matrix of step (B) in cell culture medium comprising a Rho-associated kinase inhibitor (ROCKi) and FGF-2;
(D) culturing the forming BENO originating from PSCs and matrix of step (C) in cell culture medium comprising retinoic acid and one or more inhibitors of SMAD signaling to induce neurogenesis;
(E) culturing the forming BENO of step (D) in cell culture medium comprising TGF-beta and FGF-2 to enhance genesis of stromal cells and neurogenesis;
(F) culturing the forming BENO of step (E) in cell culture medium comprising TGF-beta and one or more inhibitors of notch signaling to enhance genesis of stromal cells and neurodifferentiation.

In some embodiments, the matrix does not comprise Matrigel®. In other embodiments, the matrix does not comprise Matrigel® or other components of natural origin having a non-defined composition. In preferred embodiments, the matrix comprises collagen. In most preferred embodiments, the matrix comprises type I collagen. In some embodiments, the matrix is collagen. In some embodiments, the matrix is collagen I.

In some embodiments, the BENO is produced within a 3D environment, preferably wherein the 3D environment is defined by the matrix.

In some embodiments, the stromal cells comprise glial cells.

In some embodiments, the medium of step (D) comprises at least two inhibitors of SMAD signaling, preferably wherein the inhibitors of SMAD signaling comprise noggin and SB 431542. In some embodiments, the inhibitors of SMAD signaling are noggin and SB 431542.

In some embodiments, the inhibitor of notch signaling of step F is DAPT.

In one embodiment, the inhibitors of SMAD signaling are noggin and SB 431542 and the inhibitor of notch signaling of step F is DAPT.

In some embodiments, the matrix is collagen employed at a concentration between 0.05 mg/ml and 50 mg/ml, preferably between 0.1 mg/ml and 10 mg/ml, more preferably between 0.5 mg/ml and 5 mg/ml, most preferably at a concentration of 1 mg/ml.

In some embodiments, retinoic acid is employed at an effective concentration between 0.01 µM and 100 µM, preferably between 0.1 µM and 10 µM, more preferably between 0.5 µM and 5 µM, most preferably at a concentration of 1 µM. In some embodiments, noggin is employed at an effective concentration of 0.1 ng/ml-1 µg/ml, preferably 1 ng/ml-500 ng/ml, more preferably 10 ng/ml-200 ng/ml, most preferably 50 ng/ml. In some embodiments, SB 431542 is employed at an effective concentration of 0.1 µM-1 mM, preferably 1 µM-100 µM, more preferably between 5 µM and 50 µM, most preferably 10 µM. In some embodiments, TGF-beta is employed at an effective concentration of between 0.1 ng/ml and 100 ng/ml, preferably between 0.3 ng/ml and 30 ng/ml, more preferably between 1 ng/ml and 10 ng/ml, most preferably at a concentration of 5 ng/ml. In some embodiments, FGF-2 is employed at an effective concentration of 0.1 ng/ml and 1 µg/ml, preferably between 1 ng/ml and 100 ng/ml, more preferably between 5 ng/ml and 50 ng/ml, most preferably at a concentration of 10 ng/ml. In some embodiments, DAPT is employed at an effective concentration of between 0.01 µM and 100 µM, preferably between 0.1 µM and 10 µM, more preferably between 0.5 µM and 5 µM, most preferably at a concentration of 2.5 µM.

In some embodiments, retinoic acid is employed at a concentration of between 0.5 µM and 5 µM, noggin is employed at a concentration of 10 ng/ml-200 ng/ml, SB 431542 is employed at a concentration of between 5 µM and 50 µM, TGF-beta is employed at a concentration of between 1 ng/ml and 10 ng/ml, FGF-2 is employed at a concentration of between 5 ng/ml and 50 ng/ml, and DAPT is employed at a concentration of between 0.5 µM and 5 µM.

In some embodiments, retinoic acid is employed at a concentration of between 0.5 µM and 5 µM, noggin is employed at a concentration of 10 ng/ml-200 ng/ml, SB 431542 is employed at a concentration of between 5 µM and 50 µM, TGF-beta is employed at a concentration of between 1 ng/ml and 10 ng/ml, FGF-2 is employed at a concentration of between 5 ng/ml and 50 ng/ml, DAPT is employed at a concentration of between 0.5 µM and 5 µM, and the matrix is collagen employed at a concentration between 0.1 mg/ml and 10 mg/ml.

In some embodiments, retinoic acid is employed at a concentration of 1 µM, noggin is employed at a concentration of 50 ng/ml, SB 431542 is employed at a concentration of 10 µM, TGF-beta is employed at a concentration of 5 ng/ml, FGF-2 is employed at a concentration of 10 ng/ml, and DAPT is employed at a concentration of 2.5 µM.

In some embodiments, retinoic acid is employed at a concentration of 1 µM, noggin is employed at a concentration of 50 ng/ml, SB 431542 is employed at a concentration of 10 µM, TGF-beta is employed at a concentration of 5 ng/ml, FGF-2 is employed at a concentration of 10 ng/ml, DAPT is employed at a concentration of 2.5 µM, and the matrix is collagen employed at a concentration between 0.5 mg/ml and 5 mg/ml In some embodiment, the PSCs are animal cells. In some embodiment, the PSCs are mammal cells. In some embodiment, the PSCs are rodent (e.g., mouse or rat) or human cells. In preferred embodiments, the PSCs are human PSCs. The PSCs of the present invention are not produced using a process involving a modification to the germ line genetic identity of a human being or involving a use of a human embryo for industrial or commercial purposes.

The different steps of the invention are performed for various periods. In one embodiment, step (A) and step (B) are performed on day −1. In one embodiment step (C) is performed from day −1 to day 0. In one embodiment step (D) is performed from day 0 to day 8. In one embodiment step (E) is performed from day 8 to day 15. In one embodiment step (F) is performed from day 15 to at least day 28. In one embodiment, step (A) and step (B) are performed on day −1 and step (C) is performed from day −1 to day 0. In one embodiment, step (A) and step (B) are performed on day −1, step (C) is performed from day −1 to day 0 and step (D) is performed from day 0 to day 8. In one embodiment step (A) and step (B) are performed on day −1, step (C) is performed from day −1 to day 0, step (D) is performed from day 0 to day 8, and step (E) is performed from day 8 to day 15. In one embodiment, step (A) and step (B) are performed on day −1, step (C) is performed from day −1 to day 0, step (D) is performed from day 0 to day 8, step (E) is performed from day 8 to day 15 and step (F) is performed from day 15 to at least day 28. In one embodiment, step (A) and step (B) are performed on day −1, step (C) is performed from day −1 to day 0, step (D) is performed from day 0 to day 10, step (E) is performed from day 10 to day 15 and step (F) is performed from day 15 to at least day 28.

In one aspect, the invention provides neuronal organoids, e.g., bioengineered neuronal organoids (BENOs), characterized in that the neuronal cells of the neuronal organoid are organized in a functional neuronal network. In one aspect, the invention provides bioengineered neuronal organoids (BENOs) produced by the method of the invention.

In some aspects, the invention is directed at the use of BENOs produced by methods of the invention as model for a disease. In some embodiments, the invention is directed at the use of BENOs produced by methods of the invention as models for a disease related to neural tissue. In some embodiments, the invention is directed at the use of BENOs produced by methods of the invention as models for a disease selected from the group consisting of stroke, brain inflammation disorders, neurodegenerative diseases, neuroinflammatory diseases, traumatic injury, channelopathy, and psychiatric diseases. In some embodiments, the invention is directed at the use of BENOs produced by methods of the invention as models for a disease selected from the group consisting of neurodegenerative diseases (such as Parkinson's disease, Alzheimer's disease), neuroinflammatory diseases (e.g., multiple sclerosis), traumatic injury (e.g., brain-surgery-induced injury), channelopathy (e.g., epilepsy) and psychiatric diseases (e.g., autism, schizophrenia).

In other aspects, the invention is directed at the use of BENOs produced by methods of the invention as model for a disease, wherein the BENOs are in co-culture with another tissue engineering platform. In some embodiments, the other tissue engineering platform is selected from the group consisting of EHM (Engineered Heart Muscle), BSMs (bio-engineered skeletal muscle), ESM (Engineered Skeletal Muscle), ELT (Engineered Liver Tissue), and ECT (Engineered Connective Tissue). In other embodiments, the other tissue engineering platform is selected from the group consisting of tumor models (e.g., tumor brain invasion, metastases spread) and leukocyte infiltration models (e.g., autoimmune disease).

In some aspects, the invention is directed at the use of BENOs produced by methods of the invention in drug screening, such as drug discovery and drug refinement by phenotypic drug screening. This use of BENOs includes, but is not limited to the discovery and refinement of drugs that may induce or enhance repair, regeneration, protection, and disease prevention in brain and neural tissue.

In other aspects, the invention is directed at a kit for practicing a method of the invention. In some embodiments, the kit contains PSCs, a matrix, suitable media and the required supplements (ROCKi, FGF-2, retinoic acid, one or more inhibitors of SMAD signaling, TGF-beta, and one or more inhibitors of notch signaling). In other embodiments, a kit contains a matrix, suitable media and the required supplements (ROCKi, FGF-2, retinoic acid, one or more inhibitors of SMAD signaling, TGF-beta, and one or more inhibitors of notch signaling). In other embodiments, a kit contains a matrix and the required supplements (ROCKi, FGF-2, retinoic acid, one or more inhibitors of SMAD signaling, TGF-beta, and one or more inhibitors of notch signaling). In other embodiments, a kit contains a matrix and at least 4 of the required supplements (ROCKi, FGF-2, retinoic acid, one or more inhibitors of SMAD signaling, TGF-beta, and one or more inhibitors of notch signaling).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2. Enhanced neurogenesis under dual SMAD signaling pathway inhibition.

FIG. 3. FGF-2 enhances neuronal differentiation.

FIG. 6. Evaluation of neurogenic and gliogenic potential of different protocols.

FIG. 7. Heat maps from RNAseq analysis during the time course of development displaying RNAseq data on neurogenesis and maturation in BENOs.

FIG. 9. BENOs contain inhibitory and excitatory neurons.

FIG. 11. Optimal duration of incubation with NCM and NPEM.

DETAILED DESCRIPTION OF THE INVENTION

Definitions

Figure 1:
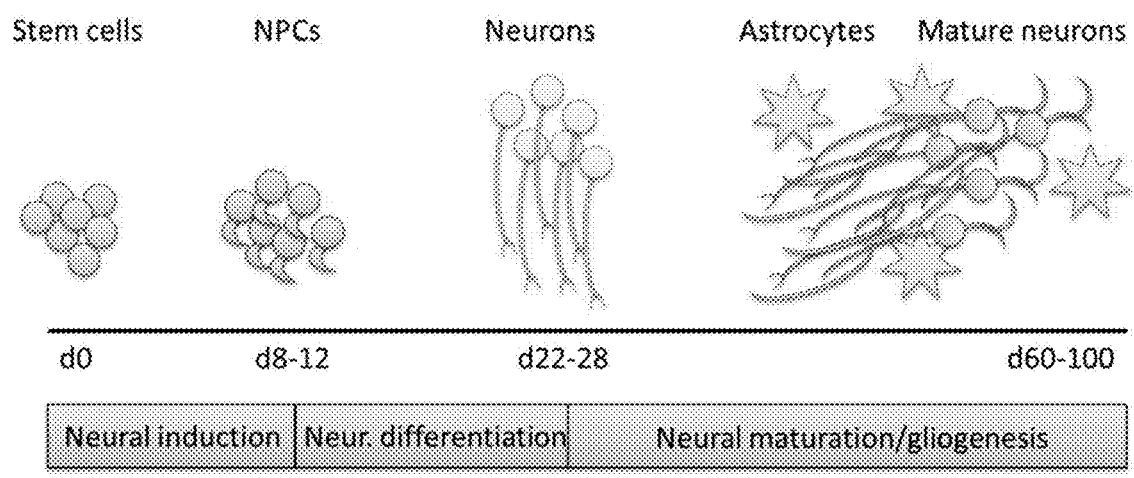
FIG. 1. Scheme of typical neural differentiation from stem cells.

As used herein, the term "organoid" refers to a tissue culture forming a three-dimensional assembly, which mimics, at least partially, the structure and/or function of an organ, such as a human organ. Organoids can be generated from pluripotent stem cells in, for example, a three-dimensional (3D) environment. One such 3D environment for organoids is a spheroid-shaped 3D environment. An organoid may further be regarded as a miniaturized and simplified version of an organ.

As used herein, the term "bioengineered neuronal organoid" (BENO) is an organoid derived from neural tissue that has been produced according to the methods of the present invention. A BENO may be regarded as a miniaturized and simplified model of a neural organ, including the brain, or of neural tissue existing within an organ or controlling an organ, for instance, neural tissue present within the heart (e.g., sympathetic nervous system) and skeletal muscle (e.g., nicotinergic nerve endings at skeletal neuromuscular junctions).

A "forming BENO" as used herein is a composition of cells and matrix that is in the process of developing into a BENO. A forming BENO is characterized in that its cellular and matrix material has been subjected to step C of the methods of the invention, but either has not yet been subjected to step F of the methods of the invention or step F is not yet finished.

The term "3D environment" as used herein represents a structure extending in all three dimensions of space. In the context of a cell culture, a 3D environment corresponds to a structure wherein cells are arranged in a three dimensional space in relation to each other. One example of a 3D environment is a spherical arrangement. Different from a 3D environment is a 2D environment, wherein the cells are arranged in a single layer, for example there is no difference in one of the dimensions of the spatial relationship between the cells.

The term "3 D cell culture system" as used herein refers to cell culturing in a 3 D environment, at least initially defined by a 3D matrix.

As used herein, the term "pluripotent stem cells" (PSCs) are cells having the property of self-replication, and a propensity to differentiate into cells found in the three germ layers (endoderm, ectoderm and mesoderm). PSCs exist in an undifferentiated state and are characterized by abundant expression of stemness factors such as Oct-3/4, SSEA-4, and TRA1-60, a property of self-replication, and a propensity to differentiate into cells of the three germ layers (endoderm, ectoderm and mesoderm). PSCs can be derived from numerous sources, including but not limited to, induced pluripotent stem cells (iPSCs), parthenogenetic stem cells, stem cells generated by nucleus transfer and embryonic stem cells (ESCs) and combinations thereof. ESCs can be from existing ESC lines. The PSCs of the present invention are not produced using a process involving a modification to the germ line genetic identity of a human being or involving a use of a human embryo for industrial or commercial purposes. PSCs further include PSC cell lines. The origin of PSCs as used herein is not particularly limited, but mammal-derived cells are preferred, more preferably the cells are of human origin.

As used herein, the term "reprogramming" refers to methods wherein a more specialized cell or a cell in some other form of advanced stage of development can be converted into a pluripotent cell.

The term "differentiated cell" as used herein refers to a cell that has developed from an unspecialized precursor phenotype to a specialized phenotype, For example, an embryonic cell can differentiate into an epithelial cell lining of the intestine, For example, differentiated cells can be isolated from a fetus or from a live animal.

"Induced pluripotent stem cells" (iPSCs) as used herein represent a type of pluripotent stem cell artificially derived from a non-pluripotent cell, typically an adult somatic cell. Induced pluripotent stem cells are considered to be similar, if not identical to, natural pluripotent stem cells, including embryonic stem cells, for instance, in terms of the expression of certain stem cell genes and proteins, chromatin methylation patterns, doubling time, embryoid body formation, teratoma formation, viable chimera formation, and potency and differentiability.

The term "neural progenitor cells" (NPCs) as used herein refers to cells derived from PSCs that have an ability to undergo cellular proliferation, to regenerate exact copies of themselves (self-renew), and to generate cellular progeny of uniquely differentiated cells. The progeny of NPCs can be either neuronal cells (such as neuronal precursors or mature neurons) or glial cells (such as glial precursors, mature astrocytes, or mature oligodendrocytes). NPCs do not normally produce progeny of other embryonic germ layers when cultured by themselves in vitro unless, for example, they are dedifferentiated or reprogrammed in some fashion. Different from stem cells like PSCs, NPCs have limited proliferative ability and thus do not exhibit an ability of self-maintenance.

The term "Matrigel®" as used herein is a composition derived from Engelbreth-Holm-Swarm mouse sarcomas (Kleinman et al., Biochemistry, 1982). Matrigel® is a mixture that is not precisely defined chemically, but generally comprises laminin, collagen IV, heparin sulfate proteoglycans, entactin, and growth factors. Matrigel® is commonly used as a matrix for cell cultivation.

The terms "chemically well-defined" or "well-defined" as used herein refer to compositions for which the chemical composition is known in a sufficient degree of accuracy. For example, at most 10%, preferably at most 5%, of the total content of the composition is chemically uncharacterized or varying in different samples of the composition.

"Components of natural origin having a non-defined composition" as used herein relates to compositions that have been isolated from natural sources (cells or tissues from animals, plants, fungi, and protists cells or viruses) that are chemically not precisely defined. For example, at least 10% of the total content of the composition must be uncharacterized or varying in different samples of the composition. Examples for components of natural origin having a "non-defined composition" include sera and Matrigel®.

The term "Fibroblast growth factor-2" (FGF-2) as used herein is a member of the fibroblast growth factor family. FGF-2 is encoded by the FGF2 gene. FGF-2 is also referred to as "basic fibroblast growth factor (bFGF)." The terms FGF-2 and bFGF are used interchangeably herein.

A "neuronal network" as used herein represents a group of one or more interconnected neurons. The connection between the neurons in a neuronal network permits a transmission of information from one neuron to the other(s). In a neuronal network, the connection between neurons can be via synapses. The presence of a neuronal network can be readily confirmed, for example, through the use calcium imaging of the neurons.

"Neuronal network organization" as used herein refers to the organization of a group of neurons as a neuronal network. This organization of neurons as a neuronal network can create a hierarchical network.

A "functional neuronal network" as used herein refers to a neuronal network, which displays a transmission of electrochemical information from one neuron to the other. Functional neuronal networks require the formation of functional synapses. Functional neuronal networks are characterized by activity patterns of the network which may include synchronized electrical activity of more than one neuron of the network or patterns showing functional interdependencies between neurons of the network, including neuron activation or inhibition patterns. The presence of a neuronal network can be confirmed, for example, by calcium imaging of the neurons. In particular, the reaction of a group of neurons to signaling molecules or inhibition of receptors of signaling molecules (e.g., GABA receptors) can confirm the presence of a functional neuronal network. One example evidencing a functional neuronal network is where the neurons in the network demonstrate synchronized calcium signals (e.g., calcium spikes), which become un-synchronized following the addition of a receptor inhibitor that inhibits a neuronal signaling molecule and subsequently re-synchronize upon inhibitor removal.

"Neuronal network function" as used herein is the transmission of electrochemical information from one neuron to the other.

The term "inducing" as used herein means initiating and/or enhancing a particular physiological effect such as cell proliferation or cell differentiation.

"Neurogenesis" as used herein refers to the differentiation and/or proliferation of cells towards fully differentiated neural cells which are not able to differentiate further. As such, neurogenesis includes the differentiation of PSCs to NPCs, the proliferation of NPCs, the differentiation of NPCs into more differentiated neural cells, for instance, either neuronal cells (such as neuronal precursors or mature neurons) or glial cells (such as glial precursors, mature astrocytes, or mature oligodendrocytes), or the proliferation of more differentiated neural cells.

The term "neurodifferentiation" as used herein means the differentiation of neural cells towards fully differentiated neural cells which are not able to differentiate further. As such, neurodifferentiation includes the differentiation of NPCs into more differentiated neural cells, for instance, either neuronal cells (such as neuronal precursors or mature neurons) or glial cells (such as glial precursors, mature astrocytes, or mature oligodendrocytes), or the differentiation of more differentiated neural cells into even more differentiated neural cells, for instance, from neuronal precursors to mature neurons.

"Embedding of cells in a matrix" as used herein refers to the interaction of cells with, and/or the attachment of cells to, a matrix. This process is regulated by cell-matrix interaction, for instance, through cellular receptors including integrins.

The term "matrix" as used herein means a material that can create a 3D environment suitable for embedding cells. Preferably, the matrix of the instant invention forms a hydrogel structure. Exemplary suitable matrices include collagen or synthetic collagen mimics.

"Hydrogel" as used herein refers to a network of hydrophilic polymers comprising water, but not being water-soluble. Hydrogel molecules are chemically and/or physically connected, for example, by covalent or ionic bonds or entanglement to thereby form a 3D environment. A hydrogel network can also be a natural or synthetic polymeric network.

The term "stromal cells" as used herein refers to neural cells that are not neuronal cells. In particular, exemplary stromal cells include glial cells, such as glial precursors, mature astrocytes, or mature oligodendrocytes.

The term "signaling" as used herein refers to the transmission of information (signals) within a cell or between two or more cells. The signaling transmission can occur by chemical reaction means (such as phosphorylation, protein cleavage), through a release of signaling molecules (including ions, neurotransmitter), or alternatively, through changes in the immediate electrochemical potential.

"Tissue engineering platform" as used herein means an in-vitro assembly of cells that is designed to mimic structural and/or functional features of tissue, preferably human tissue.

The term "phenotypic drug screening" as used herein refers to screening of the applicability of new or existing drugs based on their effect on a phenotype of a model system.

The term "bioengineering" and "bioengineered" as used herein refers to methods to manipulate biological systems and biological material. Examples for bioengineering are molecular cloning, transfection, transduction, and influencing cells using chemicals or other materials.

The term "disease modeling" as used herein refers to the process of generating a model for a disease that mimics some or all features of the disease, at least partially. Diseases models can be used to assess the influence of compounds such as drugs on the diseases or some features of the disease. Exemplary disease models are cell cultures, organoids and mouse models.

All terms that are not specifically defined herein are to be understood according to the customary meaning in the fields of biology and medicine, specifically, in the areas stem cell and organoid research.

Principle of the Invention

The present invention provides methods for producing bioengineered neuronal organoids (BENOs) under chemically defined conditions, which are reproducible and result in a consistent product. Staged SMAD and notch inhibition in the presence of retinoic acid and FGF-2 for enhanced neurogenesis with TGF-beta for supporting gliogenesis represents a unique combination of biological activities for neurogenesis in a matrix environment, resulting in the formation of functional neuronal networks. One exemplary suitable matrix of the invention is a collagen hydrogel. At the time of the present invention, it could not be predicted whether neuro- and gliogenesis could be controlled using defined factors in a matrix environment that is not itself inducing neurogenesis; in contrast to, for example, a Matrigel® matrix, which is known to induce neurogenesis since its introduction by Kleinman and colleagues in the 1990's (e.g., Jucker et al., *J Neurosci Res.* 1991)

The methods of the present invention were developed through several iterations, for instance, as disclosed by Example 1, resulting in structures displaying pronounced neuronal network organization and function, which is supported by co-developing stroma cells such as glia. The network organization and function, for example, the formation of functional synapses between different neuronal cells (and thus, a functional hierarchy as described in Example 5) of the neuronal organoids disclosed herein offer a number of advantages over conventional organoid structures. In particular, the neuronal organoids disclosed herein can be produced show high consistency due to defined culturing conditions, comprise functional neuronal networks and can be produced in short time frames (e.g., 29 days from mixing of PSCs and matrix).

The presently disclosed methods of the invention comprise a number of steps for implementation. These steps are:
(A) providing a source of PSCs;
(B) culturing the PSCs of step (A), embedded in a matrix immersed in cell culture medium;
(C) culturing the PSCs in said matrix of step (B) in cell culture medium comprising a Rho-associated kinase inhibitor (ROCKi) and FGF-2;
(D) culturing the forming BENO originating from PSCs and matrix of step (C) in cell culture medium comprising retinoic acid and one or more inhibitors of SMAD signaling to induce neurogenesis;
(E) culturing the forming BENO of step (D) in cell culture medium comprising TGF-beta and FGF-2 to enhance genesis of stromal cells and neurogenesis;
(F) culturing the forming BENO of step (E) in cell culture medium comprising TGF-beta and one or more inhibitors of notch signaling to enhance genesis of stromal cells and neurodifferentiation.

Providing Pluripotent Stem Cells (PSCs), (Step A)

The present invention relates to producing bioengineered neuronal organoids (BENOs) from pluripotent stem cells (PSCs). Pluripotent stem cells can be obtained from a variety of sources, including but not limited to, induced pluripotent stem cells (iPSCs) (which can be generated by a reprogramming of cell types including fibroblasts, keratinocytes, bone marrow derived cells or blood derived cells such as cord blood derived cells), parthenogenetic stem cells, stem cells generated by nucleus transfer, and embryonic stem cells and/or mixtures thereof. The PSCs of the present invention are not produced in a process that involves modifying the germ line genetic identity of a human being or which involves the use of a human embryo for industrial or commercial purposes. The methods of the invention can also be performed using PSC cell lines, for example, the iPSC-G1 cell line described in Tibury et al., Circulation, 2017.

PSCs are characterized by an abundant expression of stemness factors such as Oct-3/4, SSEA-4, and TRA1-60 in an undifferentiated state, a property of self-replication, and a propensity to differentiate into cells of the three germ layers (endoderm, ectoderm and mesoderm). The PSCs can also be induced PSCs (iPSCs).

Prior to use in the presently claimed methods, PSCs are cultured under appropriate conditions known in the art. PSCs may be, as necessary, cultured according to a standard maintenance procedure, e.g., growth on a maintenance support such as Matrigel®. PSCs are grown in any appropriate cell culture medium known in the art. An exemplary cell culture medium is TeSR™-E8™ Basal medium (Stemcell), optionally comprising Rho-associated protein kinase inhibitor (ROCKi), e.g., at a concentration of 5 µM or 10 µM. TeSR™-E8™ medium refers to a commercially available feeder-free culture medium useful for human embryonic stem (ES) cells and human induced pluripotent stem cells (iPSCs). Exemplary culturing methods for PSCs are reported in Stover and Schwartz, *Methods Mol Biol.* 2011.

In using PSCs for the present invention, the PSCs are detached from their maintenance support, e.g., Matrigel®, for instance via EDTA treatment. EDTA can be used at a concentration of 0.1-10 mM, preferably between 0.5 and 2 mM. The EDTA treatment is performed for 1-10 minutes, preferably between 4-6 minutes. Preferred EDTA treatment conditions are 0.5 mM EDTA for 5-10 minutes at room temperature and 2 mM EDTA for 5-8 minutes at room temperature.

Culturing the PSCs Embedded in a Matrix Immersed in Cell Culture Medium ("Step B")

The provided PSCs described above are subsequently cultivated with a matrix, which allows embedding of the PSCs into a 3D environment that is defined by the matrix. The embedding and self-organization of PSCs within such a 3D environment provides the basis for the organoid of the invention to be generated. Preferably, the cells should be embedded in the matrix in a homogenous manner.

The matrix of the invention constitutes a 3D environment that facilitates self-organization and differentiation of the PSCs and cells derived from PSCs. The structure of the matrix is stabilized by interactions of the individual matrix molecules, e.g., protein-protein interactions. Most preferably, the matrix of the invention forms a hydrogel structure.

Exemplary suitable matrices of the present invention are collagens, collagen mimics, alginate, fibrin, Matrigel®, and chitosan. Preferred matrices are collagen and collagen mimics. Most preferred matrices are based on collagen type I. Matrices based on collagen type I may contain traces of other collagens such as collagen type III. Preferably, matrices based on collagen type I contain more than 80%, more than 85%, more than 90%, more than 95%, or 100% of collagen type I.

In a preferred embodiment, the matrix of the present invention does not comprise Matrigel®. In more preferred embodiments, the present matrix does not comprise Matrigel® or other components of natural origin having a non-defined, or ill-defined composition of one or more components. This is particularly important since the use of a non- or ill-defined chemical mixture, such as Matrigel®, inevitably results in larger phenotypic variations of the generated organoids. This observation has been confirmed by, for example, Tiburcy et al., Circulation, 2017. It is well known that Matrigel® is a non-defined mixture comprising laminin, collagen IV, heparin sulfate proteoglycans, entactin, and growth factor components that are derived from Engelbreth-Holm-Swarm mouse sarcomas, wherein the lot-to-lot component percentages exhibit high variability (Kleinman et al., Biochemistry, 1982).

PSCs and matrix elements are mixed in a cell culture medium appropriate for PSC culture. Examples for such cell culture media are TeSR™-E8™ Basal medium (Stemcell) and StemFlex™ Medium (Gibco). StemFlex™ Medium is a commercially available feeder-free culture medium useful for culturing human embryonic stem (ES) cells and human induced pluripotent stem cells (iPSCs). The cell culture medium can be supplemented with additional components such as FGF-2 and ROCKi. These components may enhance cell survival and proliferation in the matrix. One exemplary medium is TeSR™-E8™ Basal medium supplemented with 20 ng/ml FGF-2 and 10 µM ROCKi. Other components that may be added to the cell culture medium include DMEM cell culture medium or NaOH for pH neutralization.

The matrix (such as a collagen matrix) is employed at an effective concentration. In some embodiments, the concentration of the matrix is between 0.05 mg/ml and 50 mg/ml. In other preferred embodiments, the concentration of the matrix is between 0.1 mg/ml and 10 mg/ml. In more preferred embodiments, the concentration of the matrix is between 0.5 mg/ml and 5 mg/ml. In a most preferred embodiment, the concentration of the matrix is 1 mg/ml.

The density of the PSCs following mixture with the medium and matrix can be in the range of $0.1\text{-}10\times10^6$ cells per ml. A preferred range is $0.5\text{-}6\times10^6$ cells per ml. A more preferred range is $1\text{-}4\times10^6$ cells per ml. One exemplary suitable value is $3\times10^6$ cells per ml.

The present culturing step is performed prior to the culturing step disclosed in the following section. This culturing step (where the PSCs are embedded in a matrix; "step B") is performed before a culturing step in which the cells are cultured in cell culture medium comprising a Rho-associated kinase inhibitor (ROCKi) and FGF-2 ("step C"). The transition of step B to step C is typically characterized by addition of the components of step C to the existing cell culture medium.

In some embodiments, this culturing step B is performed for a time period of between 1 minute and 1 day. In preferred embodiments, step B is performed between 5 minutes and 5 hours. In more preferred embodiments, step B is performed between 10 minutes and 1 hour. In even more preferred embodiments, step B is performed between 15 minutes and 30 minutes. In a most preferred embodiment, step B is performed for 20 minutes.

The time point of step B is termed "day −1" by the instant protocol relating to the production of the inventive organoids.

Step B is performed in a suitable cell culture vessel. An exemplary suitable cell culture vessel is a 96-well plate with U-bottom and low attachment properties.

Step B is performed under conditions that are suitable for PSC survival. Exemplary suitable conditions are 37° C., 5% $CO_2$, for instance, in a cell culture incubator.

Culturing the PSCs in Said Matrix of Step (B) in Cell Culture Medium Comprising a Rho-Associated Kinase Inhibitor (ROCKi) and FGF-2 ("Step C")

The PSCs in the matrix of step B are cultivated in medium comprising a Rho-associated kinase inhibitor (ROCKi) and Fibroblast Growth Factor-2 (FGF-2).

Suitable ROCKi variants include Y27632 (Stemgent), Fasudil, Ripasudil, RKI-1447, GSK429286A, Y-30141, in addition to other components reviewed in Feng et al., J Med Chem., 2016). The ROCKi is employed at an effective concentration. A preferred ROCKi is Y27632. In some embodiments, the concentration of Y27632 is between 0.1 μM and 1 mM. In preferred embodiments, the concentration of Y27632 is between 1 μM and 100 μM. In more preferred embodiments, the concentration of Y27632 is between 5 μM and 50 μM. In a most preferred embodiment, the concentration of Y27632 is 10 μM.

FGF-2 (also known as bFGF) is employed at an effective concentration. In some embodiments, the concentration of FGF-2 is between 0.1 ng/ml and 1 μg/ml. In preferred embodiments, the concentration of FGF-2 is between 1 ng/ml and 100 ng/ml. In more preferred embodiments, the concentration of FGF-2 is between 5 ng/ml and 50 ng/ml. In a most preferred embodiment, the concentration of FGF-2 is 10 ng/ml. While the invention preferably employs FGF-2, the invention can also be carried out using a FGF-2 mimetic having an equal or similar signaling activity as FGF-2, which is characterized by binding to FGF-receptors to thereby cause FGF-receptor-mediated signaling, wherein such activity is at least 10% of the signaling activity of FGF-2 at each FGF-receptor.

In this culturing step C, the PSCs are cultured in a cell culture medium that is appropriate for culturing of the PSCs. Examples of suitable cell culture medium include TeSR™-E8™ Basal medium (Stemcell) and StemFlex™ Medium (Gibco).

This culturing step is performed following step B disclosed above. The transition of step B to step C is typically characterized by the addition of the components of step C to the existing cell culture medium comprising PSCs and matrix of step B. Step C is performed prior to step D, which is described below. The transition of step C to step D is characterized by a partial or complete exchange of the cell culture medium or, alternatively, addition of the components of step D to the existing cell culture medium.

In some embodiments, step C is performed for a time period of between 6 hours and 4 days. In some preferred embodiments, step C is performed between 12 hours and 3 days. In more preferred embodiments, step C is performed between 1 day and 2 days. In a most preferred embodiment, step C is performed for 1 day.

Step C should begin on day −1 of the protocol for producing organoids. Depending on its duration, this step may extend to day 0, 1, 2, or 3 of the instant protocol. In a most preferred embodiment, step C extends to day 0 of the protocol.

Step C is performed in a suitable cell culture vessel. An exemplary suitable cell culture vessel is a 96-well plate with U-bottom and low attachment properties. Generally, the cell culture vessel will not change when performing steps B and C disclosed herein.

Step C is performed under conditions suitable for PSC survival. Exemplary suitable conditions include 37° C., 5% $CO_2$, for instance, in a cell culture incubator.

Culturing Forming BENOs Originating from PSCs and Matrix of Step (C) in a Cell Culture Medium Comprising Retinoic Acid and One or More Inhibitors of SMAD Signaling to Induce Neurogenesis ("Step D")

The PSCs treated according to step C in the matrix constitute a forming BENO. This forming BENO originating from the PSCs and matrix of step C is cultivated in a medium comprising retinoic acid and one or more inhibitors of SMAD signaling pathways. Such treatment induces neurogenesis.

Retinoic acid is employed as a signaling-activating molecule. Preferably, all-trans retinoic acid [(2E,4E,6E,8E)-3, 7-dimethyl-9-(2,6,6-trimethylcyclohexen-1-yl)nona-2,4,6, 8-tetraenoic acid] is used. However, the invention can also be carried out using retinoic acid derivatives having an equal or similar signaling activity as all-trans retinoic acid, which is typically characterized by binding to the retinoic acid receptor to thereby cause retinoic-acid-receptor-mediated signaling, wherein such activity is at least 10% of the signaling activity of all-trans retinoic acid. Retinoic acid is employed at an effective concentration. In some embodiments, the concentration of retinoic acid is between 0.01 μM and 100 μM. In preferred embodiments, the concentration of retinoic acid is between 0.1 μM and 10 μM. In more preferred embodiments, the concentration of retinoic acid is between 0.5 μM and 5 μM. In a most preferred embodiment, the concentration of retinoic acid is 1 μM.

SMAD inhibitors are employed to inhibit signaling mediated by Mothers against decapentaplegic homologue (SMAD) proteins (e.g., SMAD-1-SMAD-9). Inhibition of SMAD-mediated signaling induces neurogenesis. Suitable SMAD inhibitors include the protein noggin, SB 431542 (Tocris), dorsomorphin, and LDN-193189 (Tocris). SMAD inhibitors are employed at an effective concentration. For example, noggin can be employed at a concentration of 0.1 ng/ml-1 μg/ml, preferably 1 ng/ml-500 ng/ml, more preferably 10 ng/ml-200 ng/ml, most preferably 50 ng/ml. SB 431542 can be used at a concentration of 0.1 μM-1 mM, preferably 1 μM-100 μM, more preferably between 5 μM and 50 μM, most preferably 10 μM. The use of more than one SMAD inhibitor may have positive effects on inducing neurogenesis (Example 1). One preferred combination of SMAD inhibitors comprises noggin and SB 431542. A more preferred combination of SMAD inhibitors consists of noggin and SB 431542. A most preferred combination of SMAD inhibitors consists of noggin (50 ng/ml) and SB 431542 (10 µM).

The forming BENOs are cultured in any cell culture medium appropriate for PSC culturing. Exemplary cell culture media include Stemdiff™ neuron differentiation medium (Stemcell), Neurobasal™ Medium (Gibco), and the medium used in Example 2. Stemdiff™ is a neural induction medium that is a defined, serum-free medium useful for the neural induction of human embryonic stem (ES) cells and induced pluripotent stem (iPS) cells. Neurobasal™ medium is a commercially available basal medium useful for culturing post-natal and adult neuronal cells.

Step D of the disclosed methods is typically performed after step C. The transition of step C to step D is characterized by a partial or complete exchange of the cell culture medium or, alternatively, addition of the components of step D to the existing cell culture medium. Step D is typically performed before step E, as described herein. The transition of step D to step E is characterized by a partial or complete exchange of the cell culture medium or, alternatively, addition of the step E components to the existing cell culture medium.

In some embodiments, step D is performed for a time period of between 2 days and 16 days. In some preferred embodiments, step D is performed between 4 days and 12 days. In more preferred embodiments, step D is performed between 6 days and 10 days. In a most preferred embodiment, step D is performed for 8 days. It was found that performing step D for 8 days is favorable compared to 3 or 6 days (see example 8). Performing step D for 10 days is even more favorable than 8 days, while further extension of step D did not significantly improve the results (see example 8). Therefore, in another particularly preferred embodiment, step D is performed for at least 8 days or for 10 days.

The day "designations" in performing this step depend on the duration of previously performed steps B, C and D. In general, the starting point of step D is between days 0 and 3. The end of step D is generally between day 2 and day 19. In a most preferred embodiment, step D extends from day 0 to day 8. In another particularly preferred embodiment, step D extends from day 0 to day 10.

Step D is performed using any suitable cell culture vessel. Exemplary suitable cell culture vessels include a 96-well plate with a U-bottom and low attachment properties or a 6-well plate or a custom-made 3D-printed or cast molded vessel for single or multi organoid culture. The cell culture vessel will typically not change between steps C and D. The cell culture vessel may be changed when performing step D. One such exemplary vessel change is the expansion from a 96-well plate to a 6-well plate.

Step D is performed under conditions amenable to forming BENO survival. Exemplary suitable conditions are 37° C., 5% $CO_2$, for instance, in a cell culture incubator.

Culturing the Forming BENO of Step D in Cell Culture Medium Comprising TGF-Beta and FGF-2 to Enhance the Genesis of Stromal Cells and Neurogenesis ("Step E")

The forming BENO provided following step D is cultivated in medium comprising transforming growth factor (TGF) beta and fibroblast growth factor-2 (FGF-2). Treatment with TGF-beta enhances the genesis of stromal cells, while FGF-2 enhances neurogenesis.

Treatment with TGF-beta enhances the genesis and functionality of stromal cells in the emerging organoid. The stromal cells are stromal cells of neural tissue. Exemplary stromal cells include glial cells. TGF-beta employed in the present invention can be TGF-beta 1, TGF-beta 2, TGF-beta 3, or mixtures thereof. The invention can also be carried out using a TGF-beta mimetic having an equal or similar signaling activity as TGF-beta, which is characterized by binding to a TGF-beta receptor to thereby cause TGF-beta-receptor-mediated signaling, wherein such activity is at least 10% of the signaling activity of TGF-beta 1. Preferably, TGF-beta employed in the present invention is TGF-beta 1. TGF-beta is employed at an effective concentration. In some embodiments, the concentration of TGF-beta is between 0.1 ng/ml and 100 ng/ml. In preferred embodiments, the concentration of TGF-beta is between 0.3 ng/ml and 30 ng/ml. In more preferred embodiments, the concentration of TGF-beta is between 1 ng/ml and 10 ng/ml. In a most preferred embodiment, the concentration of TGF-beta is 5 ng/ml.

FGF-2 (also known as bFGF) is employed at an effective concentration. In some embodiments, the concentration of FGF-2 is between 0.1 ng/ml and 1 µg/ml. In some preferred embodiments, the concentration of FGF-2 is between 1 ng/ml and 100 ng/ml. In more preferred embodiments, the concentration of FGF-2 is between 5 ng/ml and 50 ng/ml. In a most preferred embodiment, the concentration of FGF-2 is 10 ng/ml. While the invention preferably employs FGF-2, the invention can also be carried out using a FGF-2 mimetic having an equal or similar signaling activity as FGF-2, which is characterized by binding to FGF-receptors to thereby cause FGF-receptor-mediated signaling, wherein such activity is at least 10% of the signaling activity of FGF-2 at each FGF-receptor.

In this step of the disclosed methods, the forming BENO is cultured in a cell culture medium appropriate for culturing PSCs. Exemplary cell culture media include Stemdiff™ neuron differentiation medium (Stemcell), Neurobasal™ Medium (Gibco), and the medium used in Example 2.

Step E is typically performed following step D. The transition of step D to step E is characterized by a partial or complete exchange of the cell culture medium or, alternatively, addition of the components of step E to the existing cell culture medium. Step E is typically performed before step F, which is described below. The transition of step E to step F is characterized by a partial or complete exchange of the cell culture medium or, alternatively, addition of the components of step F to the existing cell culture medium.

In some embodiments, step E is performed for a time period of between 2 days and 16 days. In preferred embodiments, step E is carried out between 4 days and 12 days. In more preferred embodiments, step E is performed between 6 days and 10 days. In a most preferred embodiment, step E is performed for 7 days. It was found that performing step E for 5 days is not significantly inferior compared to 7 days; conversely, performing step E for 2 days resulted in inferior BENO condensation (see example 8). Therefore, in another particularly preferred embodiment, step E is performed for at most 7 days or for 5 days.

The day "designations" in performing this step depend on the duration of previously performed steps B, C, D and E. In general, the starting point of step E is between days 3 and 15. The end of step E is between day 5 and day 20. In a most preferred embodiment, step E extends from day 8 to day 15. In another particularly preferred embodiment, step E is performed from day 10 to day 15.

Step E is performed using any suitable cell culture vessel. Exemplary suitable cell culture vessels include a 6-well or a custom-made 3D-printed or cast molded vessel for single or multi organoid culture. The cell culture vessel will typically not change between steps D and E. The cell culture vessel may be changed when performing step E.

Step E is performed under conditions amenable to forming BENO survival. Exemplary suitable conditions are 37° C., 5% $CO_2$, for instance, in a cell culture incubator.

Culturing the Forming BENO of Step E in Cell Culture Medium Comprising TGF-Beta and One or More Inhibitors of Notch Signaling to Enhance Genesis of Stromal Cells and Neurodifferentiation ("Step F").

The forming BENO provided following step E is cultivated in medium comprising transforming growth factor beta (TGF-beta) and one or more inhibitors of notch signaling. Treatment with TGF-beta enhances the genesis of stromal cells, while inhibition of notch signaling enhances neurodifferentiation.

Treatment with TGF-beta enhances the genesis and functionality of stromal cells in the emerging organoid. The stromal cells are stromal cells of neural tissue. Exemplary stromal cells include glial cells. TGF-beta employed in the present invention can be TGF-beta 1, TGF-beta 2, TGF-beta 3, or mixtures thereof. The invention can also be carried out using a TGF-beta mimetic having an equal or similar signaling activity as TGF-beta, which is characterized by binding to a TGF-beta receptor to thereby cause TGF-beta-receptor-mediated signaling, wherein such activity is at least 10% of the signaling activity of TGF-beta 1. TGF-beta is employed at an effective concentration. In some embodiments, the concentration of TGF-beta is between 0.1 ng/ml and 100 ng/ml. In preferred embodiments, the concentration of TGF-beta is between 0.3 ng/ml and 30 ng/ml. In more preferred embodiments, the concentration of TGF-beta is between 1 ng/ml and 10 ng/ml. In a most preferred embodiment, the concentration of TGF-beta is 5 ng/ml.

Notch signaling inhibitors are employed for inhibiting cell signaling mediated by a notch receptor (e.g., notch 1-notch 4 receptors). Inhibition of notch signaling enhances neurodifferentiation. Suitable notch signaling inhibitors include N-[(3,5-Difluorophenyl)acetyl]-L-alanyl-2-phenyl]glycine-1,1-dimethylethyl ester (DAPT), Compound E (Stem cell technologies), and γ-secretase inhibitors such as those described in Olsauskas-Kuprys et al., OncoTargets and Therapy, 2013. Notch signaling inhibitors are employed at an effective concentration. A preferred notch signaling inhibitor of the present invention is DAPT. In some embodiments, the concentration of DAPT is between 0.01 µM and 100 µM. In some preferred embodiments, the concentration of DAPT is between 0.1 µM and 10 µM. In more preferred embodiments, the concentration of DAPT is between 0.5 µM and 5 µM. In a most preferred embodiment, the concentration of DAPT is 2.5 µM.

In this step of the disclosed methods, the forming BENO is cultured in a cell culture medium that is appropriate for its culturing. Exemplary cell culture media include Stemdiff™ neuron differentiation medium (Stemcell), Neurobasal™ Medium (Gibco), and the medium used in Example 2.

Step F is typically carried out following step E. The transition of step E to step F is characterized by a partial or complete exchange of the cell culture medium or, alternatively, addition of the components of step F to the existing cell culture medium.

In some embodiments, step F is performed for a time period of between 5 days and 95 days. In preferred embodiments, step F is performed between 7 days and 50 days. In more preferred embodiments, step F is performed between 10 days and 20 days. In a most preferred embodiment, step F is performed for 13 days.

The day "designations" in performing this step depend on the duration of previously performed steps B, C, D, E and F. In general, the starting point of step F is between days 4 and 35. The end of step F is between day 9 and day 100. In a most preferred embodiment, step F extends from day 15 to day 28.

Step F is performed using any suitable cell culture vessel. One exemplary suitable cell culture vessel is a 6-well plate or a custom-made 3D-printed or cast molded vessel for single or multi organoid culture. The cell culture vessel will typically not change between steps E and F.

Step F is performed under conditions suitable for forming BENO survival. Exemplary suitable conditions are 37° C., 5% $CO_2$ for instance, in a cell culture incubator.

Completion of step F of the methods disclosed herein provides a BENO. Following step F, the BENO may be further cultured or expanded under suitable conditions, depending on the desired application of the BENO. Additional culturing may lead to the development of additional features of the BENO and/or optimize neurogenesis.

Properties and Advantages of Neuronal Organoids Produced According to Methods of the Invention Neuronal organoids produced by the methods disclosed herein (i.e. BENOs) present cortical development, neurogenesis and gliogenesis. The BENOs comprise neuronal cells and stromal cells. Stromal cells (such as glia) are important for providing a neurogenesis-promoting environment that is created upon practicing the disclosed methods. Concurrent neurogenesis and gliogenesis via the defined growth factors and small molecules disclosed herein effectively reconstruct the multicellular complexity of the human brain.

Neuronal organoids produced by the disclosed methods reveal unique features that have not been previously shown. For example, the BENOs described herein form functional neuronal networks characterized by neuronal functionality, including the formation of functional synapses, the formation of hierarchical networks, GABAergic networks, and also the synchronization of neurons (Example 5). These neuronal capabilities represent at least one important advantage over conventional neuronal organoids. In particular, BENOs can comprise excitatory and inhibitory neurons and excitatory and inhibitory neuronal networks.

Moreover, BENOs produced by methods of the present invention are preferably produced under fully defined conditions (e.g., serum-free). This means that the BENOs are reliably reproducible since variations originating from non- or ill-defined chemical components is eliminated.

Application of BENOs

BENOs produced by methods of the present invention can be used for so-called phenotypic drug screening. Different from target-specific drug screening techniques, phenotypic drug screening is not focused on the binding of a candidate molecule to a specific target, but instead on the effect that a target molecule has on a phenotype. A pre-condition of such phenotypic drug screening is the presence of an appropriate model that can mimic a phenotype of the investigated disease. The presently disclosed BENOs may provide such a disease model when investigating various diseases related to neural tissues. Diseases for which the present invention can provide a suitable model for drug screening include stroke, brain inflammation disorders, neurodegenerative diseases (such as Parkinson's disease, Alzheimer's disease, per Example 6), neuroinflammatory diseases (e.g., multiple sclerosis), traumatic injury (e.g., brain-surgery-induced injury), channelopathy (e.g., epilepsy) and psychiatric diseases (including autism and schizophrenia, per Example 7).

BENOs can be used for discovery and drug refinement by phenotypic drug screening. This use of BENOs includes the discovery and refinement of drugs that may induce or enhance repair, regeneration, protection, and disease prevention in brain and neural tissue.

The PSCs useful for such BENO models can be obtained from healthy individuals or from diseased patients. Alternatively, gene editing of pluripotent stem cells can be applied to create any genetic and epigenetic modification of interest. After producing BENO compositions from the PSCs according to the presently disclosed methods, the BENOs thus allow phenotypic tissue screening with high predictive value. Due to the higher degree of maturation, cellular complexity, and hierarchical network function of neural tissues, using the BENOs according to the invention offers numerous advantages over conventional models. Moreover, the simplicity of the disclosed methods for BENO production readily enables high-throughput phenotypic screening. Healthy and disease-modelled BENOs can be subjected to simulated diseases (for example, hypoxia to induce stroke-like damage). Phenotypic read-outs include effects on tissue formation, electrical connectivity, cell death and cell proliferation in specific cell types within BENOs. A phenotypic drug screen can allow the definition and validation of a variety of drug targets. This can thus provide a basis for subsequent compound screening for identifying, e.g., compounds having regenerative, reparative, disease modifying, or protective biological activity.

BENOs produced according to the presently disclosed methods can also be used for drug safety screening to test, for instance, the potential of a substance to induce electrical disturbances (seizures), degeneration, cell death, or other cellular anomalies in neural tissue.

BENOs produced by methods of the present invention can also be used for mode of action studies involving drugs, e.g., in preclinical trials running in parallel to clinical trials.

BENOs produced by methods of the present invention can also be used for personalised medicine purposes. For example, patient-derived iPSCs can be used to simulate diseases and test personalized therapies. BENOs of the present invention could be particularly useful in testing therapies for diseases that are related to neural tissues, e.g., neurodegenerative diseases or neuroinflammatory diseases. All possible therapy options could be explored and tested using the described BENOs, e.g., therapies by drugs, biological agents like antibodies or non-coding RNAs, gene editing, or a combination thereof.

BENOs can also be applied to generate increasingly elaborate tissue models in co-cultures of BENOs with other tissue engineering platforms. In some embodiments, co-culture with EHM (Engineered Heart Muscle) and BSMs (bioengineered skeletal muscle) can be used to study neuromuscular junction development. Specifically, co-cultures of BENOs with EHM can be used to study neuron and pacemaker or neuron and cardiomyocyte interactions. This model can then be used to study arrhythmia development. In other embodiments, BENOs are co-cultured with ESM (Engineered Skeletal Muscle), ELT (Engineered Liver Tissue), or ECT (Engineered Connective Tissue). In other embodiments, BENO-tumor models are used to study tumor-brain interactions (e.g., tumor brain invasion, metastases spread) or BENO-leukocyte infiltration models are used to study neuronal inflammation (e.g., autoimmune diseases). In general, such co-culture models represent an important step towards parallel multiple organ screening for drug action and interaction. Co-culture models can be further used as models for diseases such as Parkinson's and other neurodegenerative diseases, e.g., to test their efficacy as a personalized treatment.

The BENOs of the present invention may also provide regenerative tissue for scientific or therapeutic purposes. For example, BENOs may be injured to study recovery and regeneration under drug or biophysical (e.g., electrical conditioning) treatment. Alternatively, BENOs may be constructed with specific brain functions, such as dopamine production and release to counter Parkinson's disease. Further BENOs may be connected to organs or used as machine-organ interfaces to enable control of enervated organs (e.g., control of skeletal muscle).

Kits

Kits of the present invention include components for practicing the presently disclosed methods. In some embodiments, a kit contains PSCs, a matrix, suitable media and the required supplements (ROCKi, FGF-2, retinoic acid, one or more inhibitors of SMAD signaling, TGF-beta, and one or more inhibitors of notch signaling). In other embodiments, a kit contains a matrix, suitable media and the required supplements (ROCKi, FGF-2, retinoic acid, one or more inhibitors of SMAD signaling, TGF-beta, and one or more inhibitors of notch signaling). In other embodiments, a kit contains a matrix and the required supplements (ROCKi, FGF-2, retinoic acid, one or more inhibitors of SMAD signaling, TGF-beta, and one or more inhibitors of notch signaling). In other embodiments, a kit contains a matrix and at least 4 of the required supplements (ROCKi, FGF-2, retinoic acid, one or more inhibitors of SMAD signaling, TGF-beta, and one or more inhibitors of notch signaling).

EXAMPLES

General Protocol for Production of BENOs

The following protocols provide steps useful for generating BENOs from a source of PSCs.

Materials

The following listing of materials were used in the experiments embodied in the Examples:

TeSR™-E8™ Kit, Stemcell Technologies #05940
EDTA Solution 0.5 M, pH 8, AppliChem #A4892.0500
Matrigel® (growth factor reduced), BD Bioscience #354230
Neurobasal™-A, Thermofischer #10888-022
100× penicillin/streptomycin (P/S), Thermofischer #15140-122
100× glutamine, Thermofischer #25030-024
FGF-2, Miltenyi Biotech #130-093-841
B27, Thermofischer #17504-044
N2, Thermoscientific #17502-048
DMSO, Sigma, #276855
Noggin, R&D systems #6057-NG-025
L-ascorbic acid 2 phosphate sesquimagnesium salt hydrate(ASC-2-P), Sigma #A8960-5G
All Trans Retinoic Acid, Sigma, R2625-50MG
TGF-beta 1 (TGFB1), Peprotech, #100-21
ROCKi (Y27632), Stemgent, #04-0012
SB 431542, Tocris, #1614
DAPT, Tocris, #2634
96-well plate (U-bottom, low attachment), Sarstedt #83.1837.500
T25 flask, Sarstedt #83.3910.002
6-well plate, Greiner #657160

Stock Solutions (−20° C.)

FGF-2 stock at 10 µg/ml prepared according to manufacturer's instructions
Noggin stock at 250 µg/ml prepared according to manufacturer's instructions
ASC-2-P stock at 200 mM in water TGFB1 stock at 10 µg/ml prepared according to manufacturer's instructions
ROCKi stock at 10 mM in DMSO
SB 431542 stock at 10 mM in DMSO
DAPT stock at 100 mM in DMSO
Retinoic Acid 10 mM in DMSO
Working Solutions (4° C.)
EDTA 0.5 mM Solution
Add 500 µl of the 0.5 M EDTA stock solution (pH 8.0), to 500 ml of Calcium/Magnesium-free PBS, containing 0.45 g NaCl. Sterile filter (0.22 um), aliquot and store at 4° C. for 6 months.
Matrigel® 1:30 Solution
Dilute 1 ml Matrigel® in 29 ml ice cold PBS using pre-cooled tips in order to protect Matrigel® from polymerizing. If solution is not clear store in the fridge overnight and mix again.
TeSR™-E8™ Medium
Prepared according to manufacturer's instructions, add 1% P/S
Basal Medium
Neurobasal™-A supplemented with:
1% of 100× glutamine, 1% of 100×P/S, 2% B27, 1% N2, 200 µM, ASC-2-P
Neural Commitment Medium (NCM)
Basal medium (50 ml) supplemented with:
50 ng/ml noggin (10 µl); In some experiments 10 µM SB 431542 (50 µl), 1 µM RA (5 µl) was used.
Neural Progenitor Expansion Medium (NPEM)
Basal medium (50 ml) supplemented with:
10 ng/ml FGF-2 (50 µl); In some experiments 5 ng/ml TGFB1 was used; In some experiments BDNF (20 ng/ml) and GDNF (10 ng/ml) was used.
Neural Differentiation Medium (NDM)
Basal medium (50 ml) supplemented with:
in some experiments 2.5 µM DAPT (1.25 µl); in some experiments 5 ng/ml TGFB1 (25 µl); in some experiments 2.5 µM DAPT (1.25 µl) and 5 ng/ml TGFB1 (25 µl)

Experimental Methods

Day −4 (standard maintenance culture of pluripotent stem cells, employed as an example for the preparation of cells)
Matrigel® Coating
Growth factor reduced Matrigel® 1:120 was diluted in ice cold PBS and plates were immediately coated (150 µl/cm$^2$). The coated plates were then stored in a refrigerator for a maximum of 2 weeks. Prior to use, the coated plates were disinfected with ethanol and placed at 37° C. in an incubator for 30-60 minutes.
EDTA Passaging (Volumes Given for T-25 Flask)
The cells were washed two times with 2 ml (80 µl/cm$^2$) 0.5 mM EDTA before adding 3 ml (120 µl/cm$^2$) 0.5 mM EDTA. Cells were incubated 5-10 minutes at room temperature. Some cell lines may require 2 mM EDTA treatment for 5-8 minutes when growing on Matrigel®. Following incubation, the EDTA solution was carefully aspirated. 3 ml fresh E8™ culture medium containing 10 µM ROCKi was then added to the cells, which were subsequently plated (50,000/cm$^2$) in an appropriate new flask with 5 ml of medium containing 5 µM ROCKi. E8™ medium is a commercially available, xeno-free and feeder-free culture medium specially formulated for the growth and expansion of human induced pluripotent stem cells (iPSCs). On the following day, the medium was changed to one without ROCKi.

Day −1 (Casting BENOS)
The following represents a formula for 10 BENOs of 30 µl volume/each (plus 20% volume as a pipetting reserve):
Begin with 50 µl collagen type I (from a 6.9 mg/ml stock, final concentration 1 mg/ml) with 50 µl 2×DMEM, 9.5 µl 0.1 M NaOH, and 238 µl cell suspension in E8™ medium complemented with 20 ng/ml FGF and 10 µM ROCKi containing 900,000 undifferentiated pluripotent stem cells (e.g., iPSC-G1 line; Tiburcy et al., Circulation, 2017). Cells were detached by EDTA incubation as described above. 30 µl of the suspension was then pipetted into a well of a 96-well plate (U-bottom, low attachment) and placed in an incubator at 37° C. for 20 minutes in order to enhance collagen consolidation (homogeneous cell entrapment). After 20 minutes, 250 µl E8™ with 10 ng/ml FGF and 10 µM ROCKi was added to each well and returned to the incubator.
Days 0, 1 and 2 (Medium Change)
200 µl medium is removed and 200 µl of NCM/well is added.
Day 3 (Medium Change and BENO Transfer)
10 BENOs are transferred into a 6-well plate containing 5 ml NCM using a wide-bore tip pipet.
Day 6 (Medium Change)
4 ml medium is removed and 5 ml fresh NCM per well is added.
Days 8, 10 and 13 (Medium Change)
4 ml medium is removed and 5 ml fresh NPEM per well is added when NPEM is used in the selected experimental protocol. If no NPEM is used, then the cells are maintained in Basal medium.
Days 15, 17, 20, 22, 24 and 27 (Medium Change)
4 ml medium is removed and 5 ml fresh NDM per well is added when NDM is used in the selected experimental protocol. If no NPEM is used, then the cells are maintained in Basal medium. The cells are assessed on day 28. If culture is prolonged, then the cells are maintained in Basal medium, whereby the medium is changed every second day as described above.

Example 1: Optimization of the Protocol for Production of BENOs

Figure 2A:
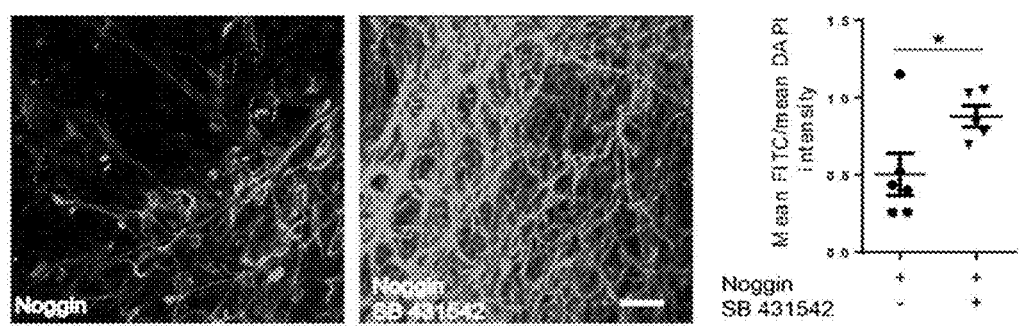
FIG. 2A. IF analysis of tissues treated exclusively with noggin or noggin and SB431542. Neurons were visualized using an antibody against neurofilament (FITC-green) and nuclei with DAPI (Blue). Bar graph represents 10 µm. Quantification of mean fluorescence ratio from whole tissues is presented in the right-hand graph.
Figure 2B:
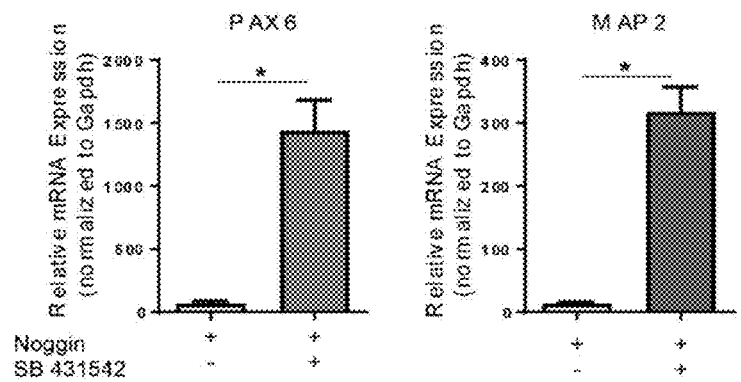
FIG. 2B. qPCR analysis of neuronal markers PAX6 and MAP2 show a 21-fold increase in both markers following SB431542 treatment (n=4 tissues/group).
Figure 3A:
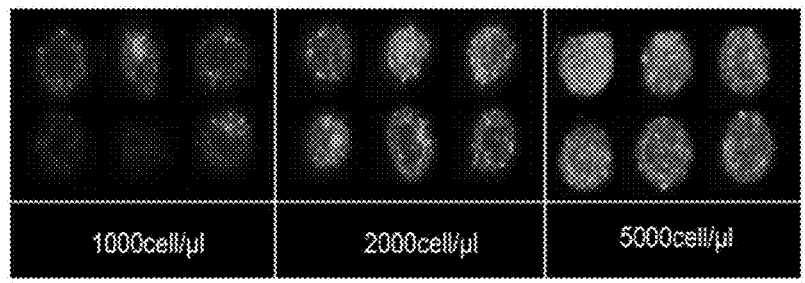
FIG. 3A. Increasing input of pluripotent stem cells resulted in enhanced neurofilament staining at BENO culture day 28.
Figure 3B:
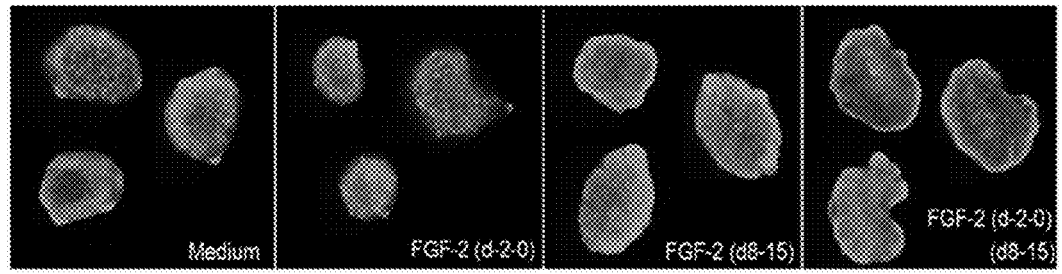
FIG. 3B. Proliferative effect of FGF-2 on stem cells and NPCs. The amount of neurons as well as network complexity inside the tissues as visualized with neurofilament staining is higher in tissues treated with FGF-2 at days 8-15.

The following studies were performed in order to optimize the disclosed protocols for neural induction, NPC amount, and neuronal differentiation. The resulting data permitted establishing of an optimal protocol for producing BENOs (Example 2).
Neural Induction Optimization
In initial attempts, single SMAD pathway inhibition (using noggin) was employed to elicit neural induction, along with the addition of retinoic acid (RA). In the present study, it was tested whether dual SMAD signaling pathway inhibition using noggin and SB431542 during the neural induction phase (days 0-8) might further enhance neurogenesis, e.g., at day 28. Accordingly, NCM containing only noggin, or NCM containing noggin and SB431542, were each investigated. Dual SMAD inhibition was clearly observed to be advantageous as to the resulting amount of maturing neurons, as demonstrated by immunofluorescence analysis (FIG. 2A) and transcript analysis of PAX6 and MAP2 (FIG. 2B).
NPC Number Augmentation
Increasing the amount of starting input pluripotent stem cells (PSCs) at the time of tissue casting resulted in a significantly higher amount of neurons (FIG. 3A). Consequently, it appears advantageous to increase the amount of neural progenitor cells (NPCs) inside the tissue by treating the organoids with FGF-2 (days 8-15). This corresponds to the use of NPEM in the above protocol. To test whether the use of FGF-2 is favorable, tissues (3000 cell/µl) were treated with 10 ng/ml FGF-2 at two different time-points; day-2 to day 0 (before neural induction at the stem cell stage), and day 8 to day 15 at the NPC stage (FIG. 3B). FGF-2 treatment at day −2-0 did not appear to provide any advantage compared to untreated tissues. However, treatment of the cells with FGF-2 at days 8-15 (i.e. NPEM use) markedly induced proliferation of the cells including NPCs, which resulted in more complex neuronal networks at day 28, as visualized by IF whole mount staining of neurofilament (FIG. 3B). Double treatment (day −2-0 and days 8-15) did not seem to be advantageous over a single treatment (days 8-15).

Neural Differentiation Optimization

Figure 4:
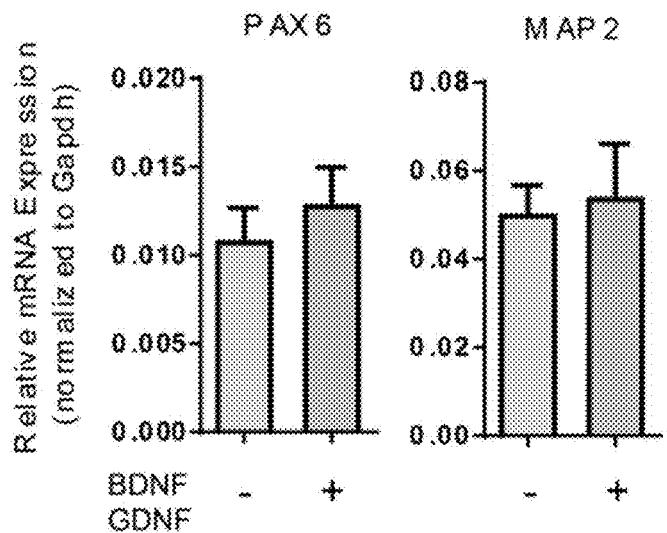
FIG. 4. Neuronal transcript analysis upon BDNF and GDNF treatment. Neither PAX6 nor MAP2 expression was enhanced upon the addition of BDNF and GDNF in culture from day 10 to day 28. BENOs were analyzed at day 28.

Numerous conventional protocols in the literature employ neurotrophic factors BDNF and GDNF to improve neuronal survival at the differentiation and maturation stages. Therefore, it was tested whether the addition of BDNF (20 ng/ml) and GDNF (10 ng/ml) to NPEM during culture days 10-28 would result in a higher number of maturing neurons by day 28 (FIG. 4).

Figure 5:
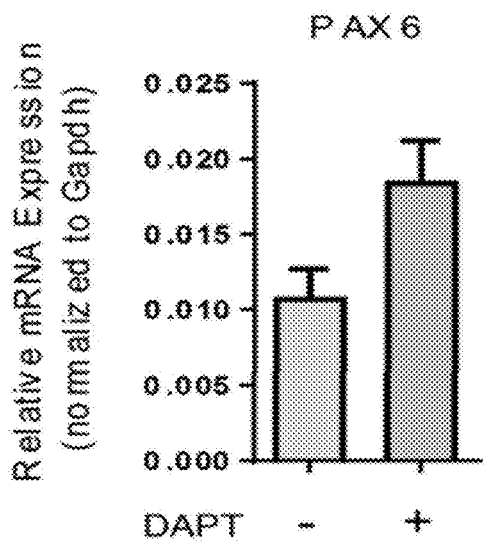
FIG. 5. Enhanced neurogenesis by notch inhibition. DAPT treatment from day 15 to day 28 increased the abundance of PAX6 transcripts, thus suggesting a higher amount of neuronal commitment.

These results demonstrate that BDNF and GDNF do not increase the amount of the neuronal marker PAX 6 or the maturation marker MAP2. Thus, treatment with BDNF or GDNF was not adopted in the protocol. On the other hand, addition of the notch inhibitor DAPT to NDM (2.5 µM, day 15-28) resulted in an increase of PAX6 transcripts, suggesting a positive effect (FIG. 5).

Optimization Experiments

Figure 6A:
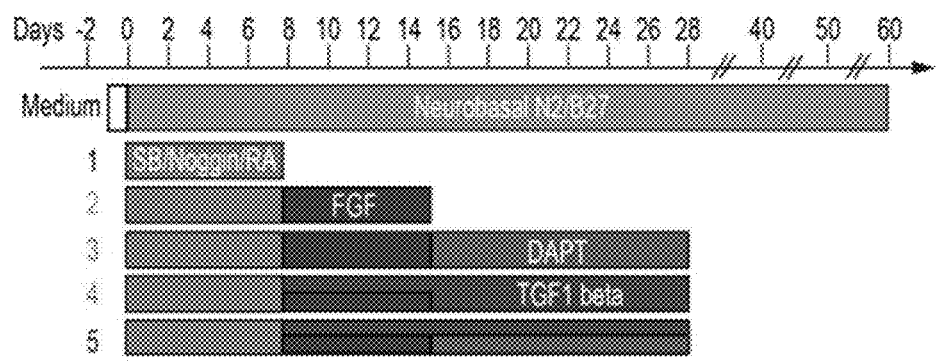
FIG. 6A. Summarizes a scheme of treatment performed in the individual protocols of Example 1.

At the final stage of optimization, for identifying the most effective protocol for neural differentiation, five different protocols were tested and compared. In all protocols, the differentiation was carried out in Neurobasal™ medium supplemented with B27 and N2. hiPS cells were subjected to neuroectoderm induction (days 0-8) under dual SMAD inhibition (noggin & SB431542) and additional retinoic acid (RA) supplementation to mimic signaling that occurs during embryonic neurogenesis. In protocol 2, the proliferative effects of FGF-2 (day 8-15) in neural progenitor cells (NPCs) were tested. In protocol 3, the effect of Notch inhibitor DAPT in neuronal commitment of NPCs (day 15-28) was tested. In protocol 4, the proliferative effects of TGF-beta 1 for glia cells (day 8-28) were tested. In protocol 5, TGF-beta 1 and DAPT treatments were combined in order to test whether development of glia and neurons can be enhanced simultaneously. The different protocols are summarized in FIG. 6A.

Figure 6B:
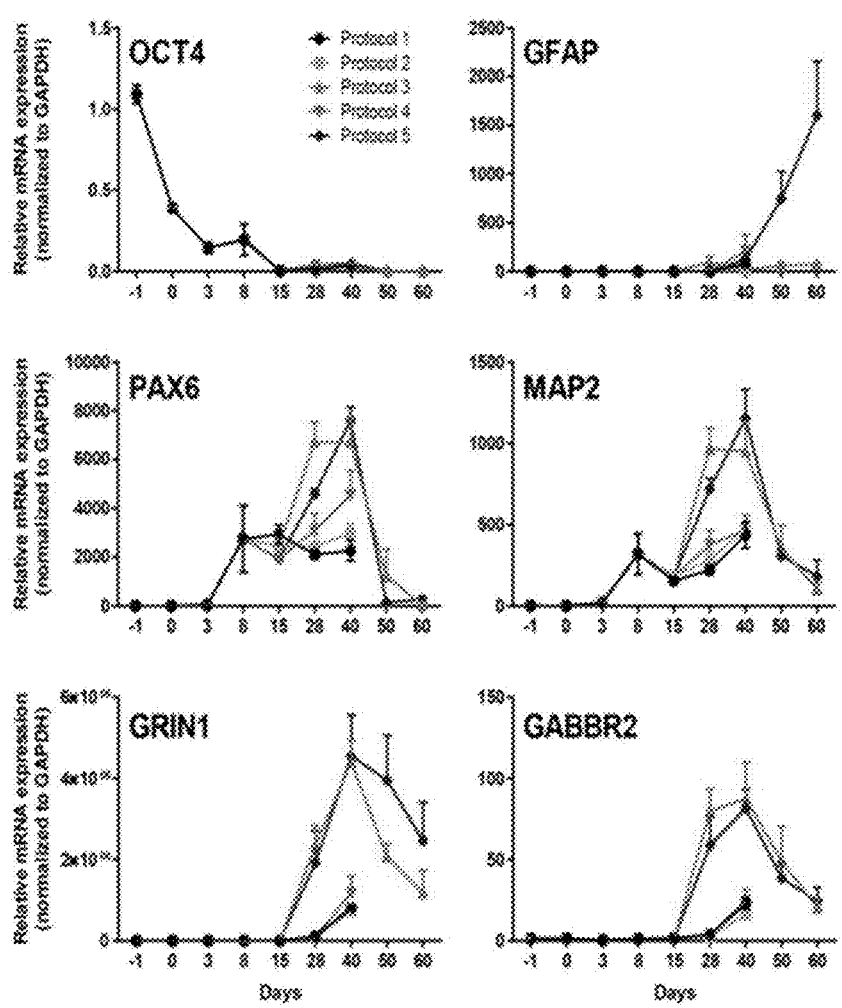
FIG. 6B. Transcriptomic time course analysis of BENO generation. OCT4 was used as stem cell marker, GFAP as a glia marker, PAX6 as NPC and neuron marker and finally MAP2, GRIN1 and GABBR2 as mature neuron marker. Data were normalized to GAPDH.

In order to assess the neurogenic and gliogenic potential afforded by the different protocols, tissues were collected at days −1, 0, 3, 8, 15, 28 and 40 (3-6 tissues/time point). Since the treatment until day 8 was identical for all protocols, tissues until that time point were only collected from protocol 1. Treatment with FGF-2 (protocol 2) did not significantly influence the level of different markers at any time point, a result that was unexpected. Treatment with DAPT (protocols 3 and 5), however, significantly increased the amount of the neuronal markers PAX6, MAP2, GRIN1 and GABBR2. Treatment with TGF-beta 1 (protocols 4 and 5) showed higher amounts of the glia marker GFAP by day 40 in comparison to the other 3 protocols (FIG. 6B). Since treatment with DAPT (protocols 3 and 5) was evidently supporting neurogenesis and TGF-beta 1 appeared to support gliogenesis, the time course analysis was extended for protocol 3 (DAPT) and protocol 5 (DAPT and TGF-beta 1). At day 50 and day 60 the expression of neuronal markers decreased with the time in both protocols, suggesting that other cell types may arise, an expected result since from day 28 the tissues are no longer undergoing treatment. Interestingly, protocol 5 clearly supported gliogenesis as evidenced by a 10-fold increase of GFAP transcripts. Collectively, the transcriptional time course analysis of the different protocols tested suggests that protocol 5 is superior to the other protocols for effectively producing neurogenesis and gliogenesis.

Figure 6C:
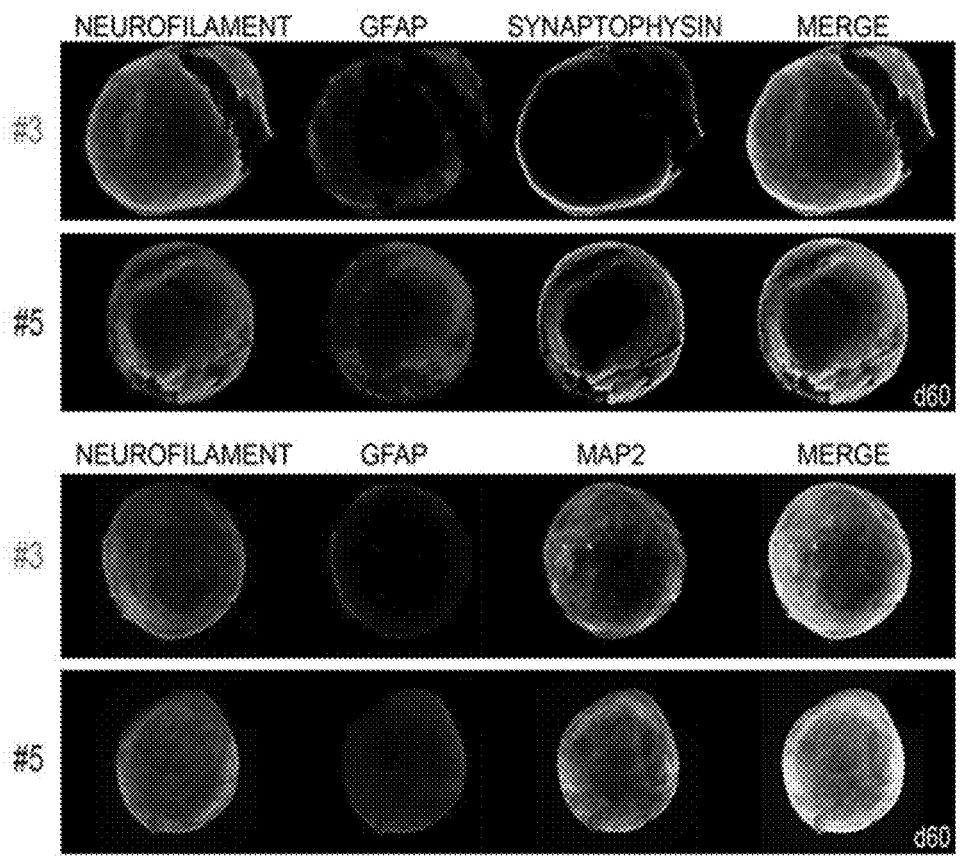
FIG. 6C. Whole mount IF analysis of BENOs at day 60. Neurofilament, MAP2, synaptophysin and GFAP were used to stain neurons, mature neurons, synapsis and glia respectively.

To validate the transcript analysis data, day 60 tissues undergoing protocol 3 and protocol 5 were stained using antibodies against neurofilament (neuron), GFAP (glia), synaptophysin (neuronal synapsis) and MAP2 (mature neurons) (FIG. 6C). Protocol 5-derived tissues contained more glia than those derived from protocol 3, whereas the amount of mature neurons appeared to be the same.

Figure 6D:
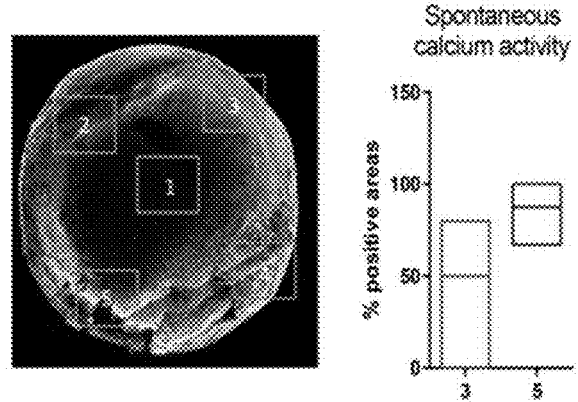
FIG. 6D. BENO activity calculated by the detection of calcium activity documented in 5 areas of the tissue.

The presence of glia is important for neuronal activity. Therefore, the initial hypothesis that BENO activity is enhanced in protocol 5 was further explored by measuring spontaneous calcium activity. To analyze this in a systematic fashion, upon staining tissues (n=3/group) with FURA-4, calcium activity was then visualized by confocal imaging in five different regions/tissue (shown in FIG. 6D). The mean calcium activity observed in each of these five areas is represented in the graph. Tissues treated with TGF-beta 1 and DAPT (protocol 5) revealed a greater number of tissue areas showing calcium activity.

To summarize, the collective data support a conclusion that, upon dual SMAD inhibition in the presence of RA, FGF-2 treatment enhances NPCs, and DAPT supports neurogenesis while TGF-beta support gliogenesis. Accordingly, the optimized differentiation protocol (Example 2) incorporates treatment using all of the above-described factors (time points indicated in FIG. 6A).

Example 2: Optimized Protocol for Generating Human Bioengineered Neuronal Organoids (BENOs)

The following studies establish an optimal protocol for producing human bioengineered neuronal organoids (BENOs).

Materials

The materials used in these experiments are the same as those used in Example 1.

Stock Solutions (−20° C.)

The stock solutions used in these experiments are the same as those used in Example 1.

Working Solutions (4° C.)

The EDTA 0.5 mM solution, the Matrigel® 1:30 solution, the TeSR™-E8™ medium, and the Basal medium used in these experiments are the same as those used in Example 1.

Neural Commitment Medium (NCM)

Basal medium (50 ml) supplemented with 10 µM SB 431542 (50 µl), 50 ng/ml noggin (10 µl), and 1 µM RA (5 µl).

Neural Progenitor Expansion Medium (NPEM)

Basal medium (50 ml) supplemented with 10 ng/ml FGF-2 (50 µl) and 5 ng/ml TGFB1.

Neural Differentiation Medium (NDM)

Basal medium (50 ml) supplemented with 2.5 µM DAPT (1.25 µl) and 5 ng/ml TGFB1 (25 µl).

Experimental Methods

Day −4 (standard maintenance culture of pluripotent stem cells, employed as an example for the preparation of cells)

The Matrigel® coating, and EDTA Passaging (for a T-25 flask) used in these experiments are the same as those used in Example 1.

Day −1 (Casting BENOS)
The same as the protocol used in Example 1.
Days 0, 1 and 2 (Medium Change)
200 μl medium is removed and 200 μl of NCM/well is added.
Day 3 (Medium Change and BENO Transfer)
10 BENOs are transferred into a 6-well plate containing 5 ml NCM using a wide-bore tip pipet.
Day 6 (Medium Change)
4 ml medium is removed and 5 ml fresh NCM per well is added.
Days 8, 10 and 13 (Medium Change)
4 ml medium is removed and 5 ml fresh NPEM per well is added.
Days 15, 17, 20, 22, 24 and 27 (Medium Change)
4 ml medium is removed and 5 ml fresh NDM per well is added. The cells are assessed on day 28. If culture is prolonged, then the cells are maintained in Basal medium, whereby the medium is changed every second day as described above.

Example 3: High Throughput Transcriptomic Analysis of BENOs

To characterize the cell types arising during the production of BENOs tissues at different time points (e.g., days −1, 0, 3, 8, 15, 28, 40, 50 and 60), the cells were submitted to RNAseq analysis; 3-6 tissues per time point).

Figure 7A:
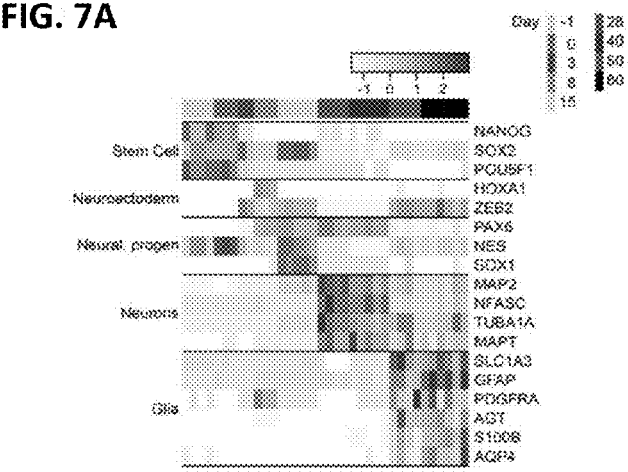
FIG. 7A. Markers depicting different state of differentiation of stem cells into neurons and glia.

First, the differentiation state of the cells during the time course of cell cultivation was tested. As expected, the stem cell markers NANOG and POUF5A1 were highly expressed at day −1 and day 0, but 3 days upon neural induction, the expression of these markers was significantly diminished. In contrast, SOX2, which is both a stem cell marker and also an NPC marker, did not show any decrease at these time points, but reached a maximum expression at day 15 along with other neuroectodermal and NPC markers. These data are consistent with the known proliferative effects of FGF-2. Most neuronal structural markers (MAP2, MAPT, NFASC, TUBA1A) increased significantly by days 28-40. Once neurogenesis was complete, gliogenesis was initiated (days 50-60). Radial glia marker PDGFR-alpha was also observed to be strongly expressed at day 8, at a time when most of the stem cells are committed to progenitor cells (FIG. 7A).

Figure 7B:
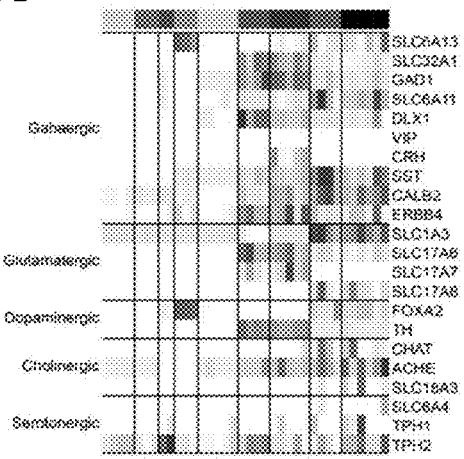
FIG. 7B. Markers of different neuronal identities.

To characterize the different types of neuronal cells present in the cell culture, specific markers expressed in serotonergic, GABAergic, glutamatergic, dopaminergic and cholinergic neurons were investigated, with the results shown in FIG. 7B. Markers for all of these neuronal types were found to be present in the neural tissues from day 28. Interestingly, although the neuronal structural transcripts were found to decrease from day 50, individual neuronal markers increased or persisted, thus suggesting that neuronal differentiation may be complete by day 40, although cellular maturation is still in progress.

Figure 7C:
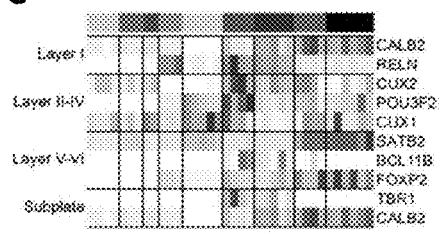
FIG. 7C. Cortical layer markers.
Figure 7D:
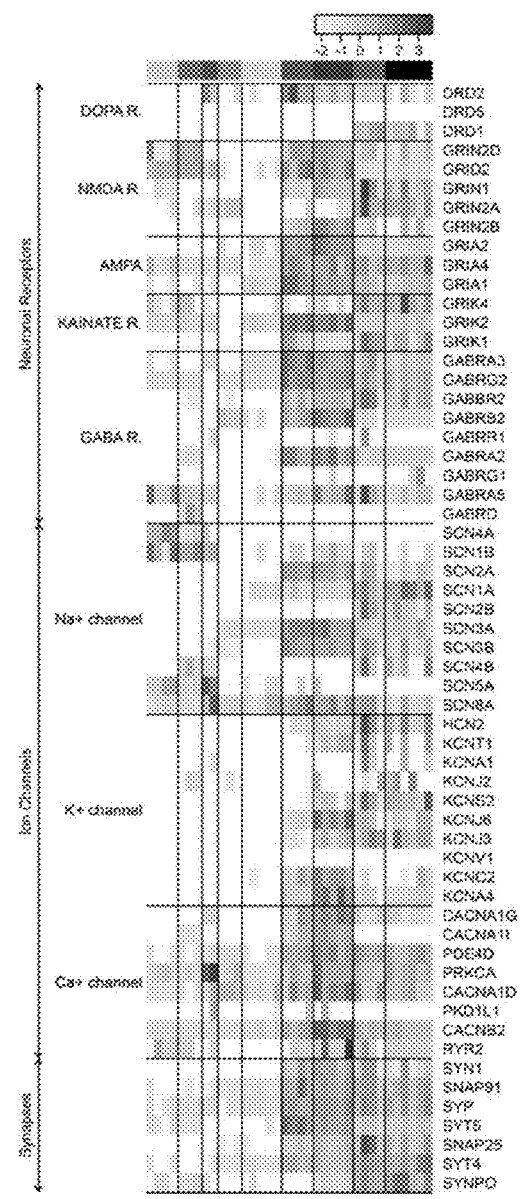
FIG. 7D. Different maturation proteins as receptors, ion channels, and synapsis related proteins. Performed in collaboration with Dr. Rashi Halder/Prof. A. Fischer (DZNE).

Similarly, analysis of the different cortical layer markers revealed that all three layers are present in the organoids (FIG. 7C).

Finally, to examine the maturation state of the neurons contained in the BENOs during the differentiation protocol, neuronal receptor expression (GABA, DOPA, Kainate, AMPA, NMDA), ion channel expression ($K^+$, $Ca^{2+}$, $Na^+$) and synaptic protein expression (SYN1, SYT4, SYP, SYNPO) were analyzed. The expression of transcripts encoding for these proteins was observed to increase at day 28, and remained stable or kept increasing until day 60. This finding supports a conclusion that although differentiation ceases by day 40, neuronal maturation and gliogenesis continued through the end of the differentiation protocol.

Figure 8:
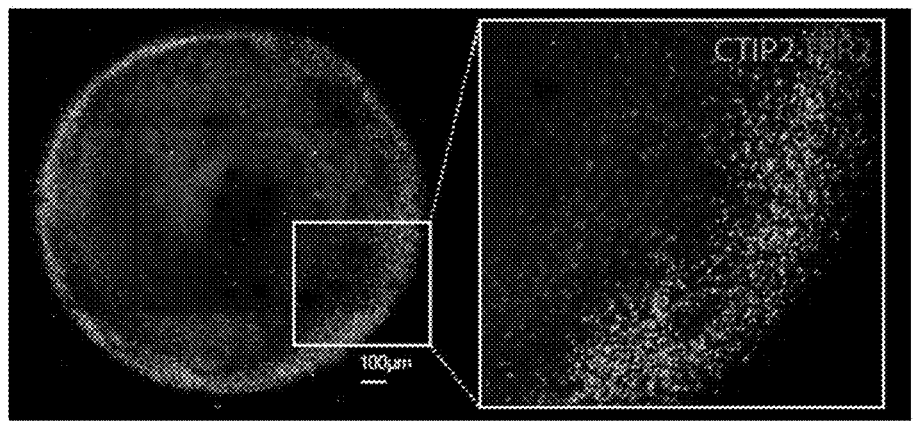
FIG. 8. Cortical layer development in BENOs. TBR2$^+$ subventricular zone progenitors are concentrically migrating from the middle of the organoid to the periphery. There, CTIP2 marks the deep layer neurons.

Example 4: Validation of Transcriptomic Analysis Findings by Whole Mount IF Analysis To verify whether the BENO model emulated normal cortical development, the markers CTIP2 (Layer V-VI neurons), TBR2 (subventricular zone precursor cells), and SOX2 (neural stem cells) were analyzed by means of immunostaining. At day 40, no SOX2 positive cells were detectable. On the other hand, TBR2 cells and CTIP2 cells were distributed concentrically in relation to each other, as observed during corticogenesis (FIG. 8).

Figure 9A:
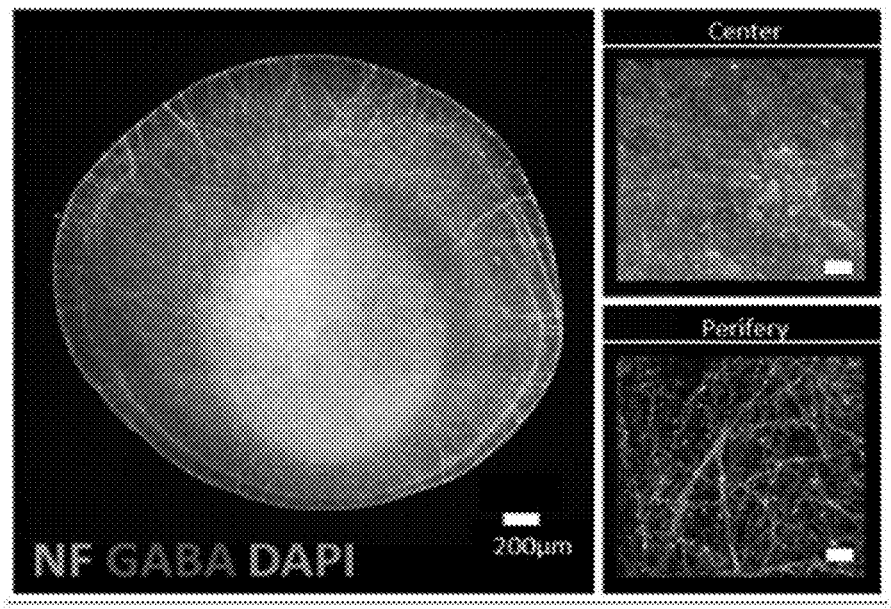
FIG. 9A. GABA is strongly expressed at the perikarya (center) and synaptic boutons in the axons of GABAergic neurons (periphery).
Figure 9B:
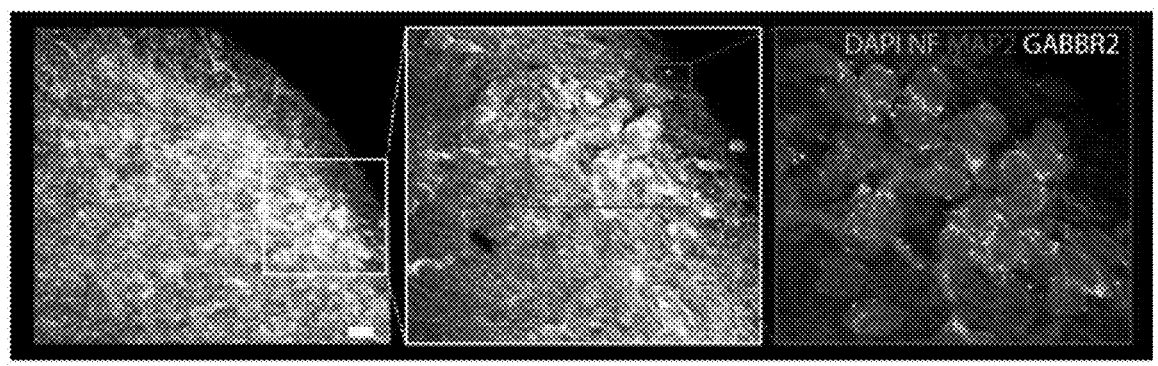
FIG. 9B. GABBR2 receptors were found expressed in neuronal perikarya (center).
Figure 9C:
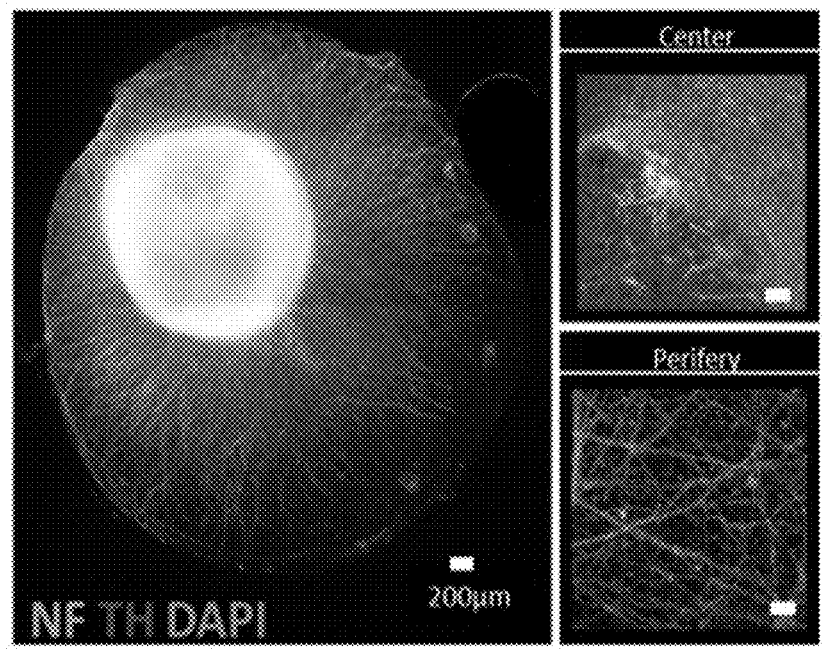
FIG. 9C. Tyrosine hydroxylase (TH) marking dopaminergic neurons was found in the center and the periphery of the organoids similar to GABA localization.
Figure 9D:
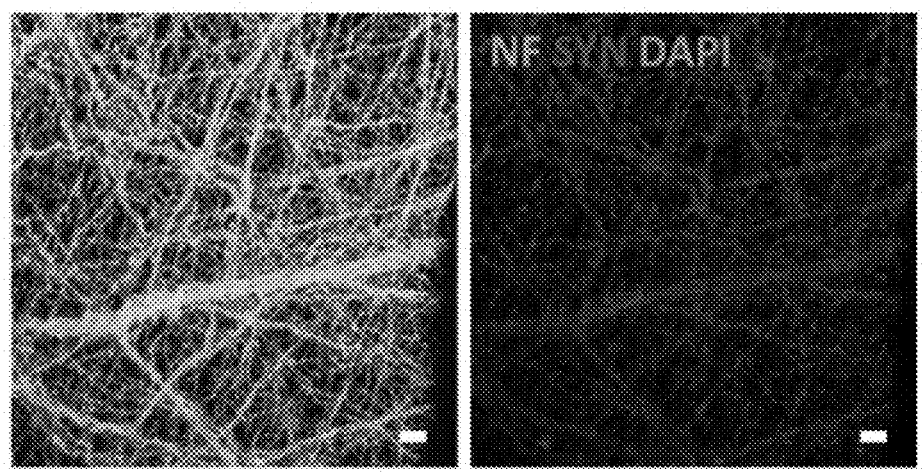
FIG. 9D. Synaptophysin staining indicated a very dense synaptic network present in the periphery of the organoid. Neurofilament, MAP2 and DAPI were used to stain axons, mature neurons and nuclei respectively. Bar graph: 10 µm unless otherwise indicated.

Using IF analysis, the strong presence of GABAergic interneurons in the BENOs was validated. Staining for both the GABAergic marker GABA and the respective receptor GABBR2 (FIG. 9A, FIG. 9B) was performed. GABA was strongly expressed in the soma compartments as well as at the synaptic boutons in the axons of GABAergic neurons. GABBR2 was observed to be expressed in neuronal perikarya. Moreover, an elaborate dopaminergic network was immunostained with TH, thereby indicating a midbrain identity. Similar to GABA, TH was detected in both soma as well as in the neuronal axons extending at the periphery of the organoid (FIG. 9C). Finally, synaptophysin staining indicated an abundance of synaptic boutons on the neurons, thus suggesting the existence of a functional neuronal network (FIG. 9D).

Example 5: Neuronal Activity: GABAergic Network

The data disclosed herein (e.g., at Examples 1-4) demonstrate that BENOs can effectively mimic normal cortical layer development, and further contain a variety of neurons and glia. The functionality of these produced neurons was subsequently investigated using calcium imaging, which can identify neuronal networks.

Figure 10:
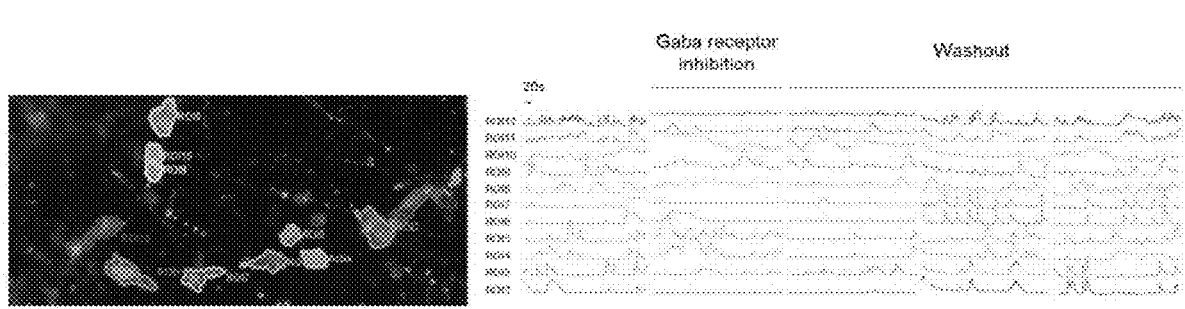
FIG. 10. Neuronal network function in BENOs suggests integrated and hierarchical synaptic functions. Fura-4 stained neurons are shown at the left panel. Matlab analysis of different regions of interest (ROI) indicated 12 different traces shown in the right panel. Before GABAR inhibition ROI (2,3), ROI (4,5), ROI (6, 7) and ROI (11,12) were synchronized. GABAR inhibition led to cell desynchronization and upon 10 min washout the cells synchronized again. Performed in collaboration with Dr. Guobin Bao/Prof. D. Schild (UMG).

To test neuronal network activity, BENOs (days 30-60) were subjected to calcium imaging under GABAergic inhibition (carried out using picrotoxin, 58 μM; saclofen, 330 μM; n=3). GABAR inhibition led to an asynchrony of previously spontaneously synchronized neurons (4 pairs of cells). Upon inhibitor washout, the same neurons re-synchronized, thereby suggesting the presence of a functional GABAergic network (FIG. 10). Functional neuronal networks did not develop in other neuronal organoids, indicating that the staged directed differentiation protocol (Example 2) for enhanced cellular complexity mimics human brain development not only in a structural sense, but also with respect to hierarchical network function.

Collectively, Examples 1-5 of the present invention convincingly demonstrate novel collagen-based, serum-free, stage-specific directed differentiation methods for the engineering of electrically active neuronal networks from human pluripotent stem cells.

Example 6: BENOs as a Model for Neuronal Regeneration

To study injury responses and tissue repair mechanisms, BENOs are exposed to injury. Cryo-, mechanical-, hypoxia-, or neurotoxin-induced global or local injury can be produced for example by a N₂-cooled metal pin, compression or dissection, culture in subcritical to 0% oxygen, as well as exposure to glutamate, dopamine, ethanol, tetrodotoxin, botulinum or tetanus toxins. Recovery from injury including cell specific responses (e.g., by neurons and glia cells) is studied specifically. Repair and regeneration for example by induction of neuronal proliferation and protection from injury for example by application of antioxidants or pharmacological modulators are studied. BENOs serve as models to identify and validate novel targets for disease modification including neuronal protection, repair, and regeneration. BENOs are used at different stages of development, e.g., as proliferating neurons (day 15, day 28 of the Example 2 protocol) and post-mitotic neurons (day 40, day 60 of the Example 2 protocol).

Example 7: BENOs as Personalized Disease Model, e.g., for Schizophrenia

BENOs are created from pluripotent stem cells, for example derived from patients by reprogramming or genetically engineered for example by CRISPR/Cas or TALEN technologies. BENOs are phenotyped as described above using means of calcium activity assessment, immunofluorescence analysis, or electrophysiological means (e.g., impaling electrode measurements, multi-electrode arrays/field potential measurements). In parallel, RNA sequencing and proteome analyses is conducted for phenotype-genotype association studies.

A use of BENOs is modeling aspects of schizophrenia. BENOs are created from iPSC cells obtained from schizophrenic patients. Subsequently, BENOs from these patients are phenotyped to analyze the phenotypic differences to healthy control subjects. Other studies are designed to investigate BENOs derived from patients suffering from autism, familiar hemiplegia and epilepsy.

Example 8: Further Optimization of Neuronal Induction and Expansion in Steps C and D To test the optimal duration of steps D and E, the protocol of example 2 was performed, only varying the duration of steps D and E (FIG. 11). Subsequently, the result of each protocol was assessed by determining mRNA expression of the neuronal marker PAX6 as a parameter for neuronal commitment.

Figure 11A:
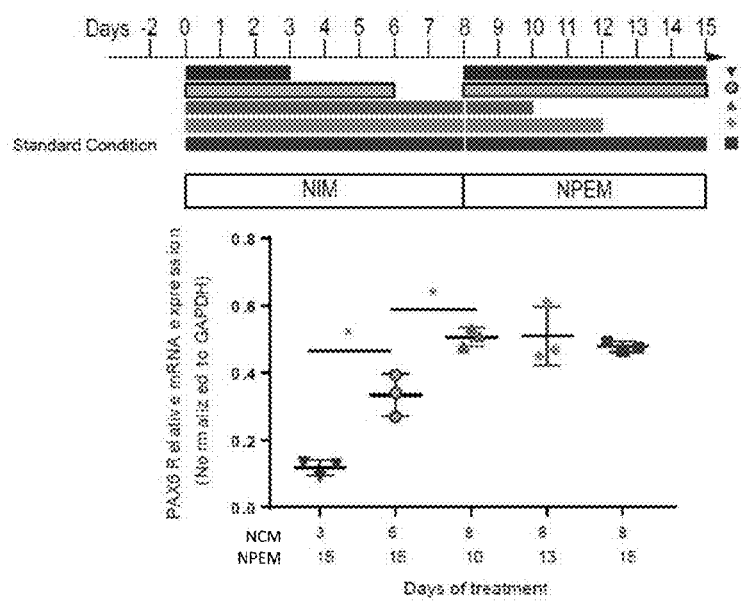
FIG. 11A. qPCR analysis of relative PAX6 transcript expression 15 days upon BENO generation using the protocols indicated in the scheme.
Figure 11B:
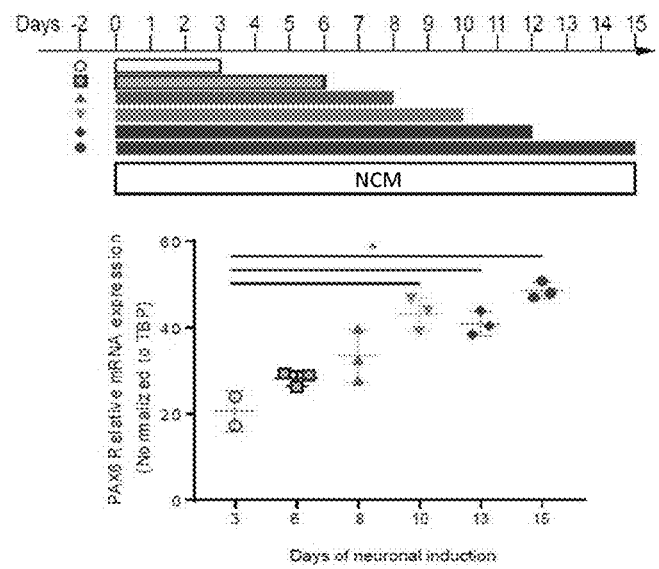
FIG. 11B. Defining the maximum duration of BENO treatment with NCM (step D). qPCR analysis of relative PAX6 transcript expression 15 days upon BENO generation using the protocols indicated in the scheme.

These experiments showed that the standard protocol of example 2, 8 days of incubation with NCM (step D), is superior to shorter incubation times like 3 or 6 days (FIG. 11A). Incubation with NCM for 10 days yielded slightly higher PAX6 mRNA expression than incubation for 8 days (FIG. 11B), while longer incubation did not increase PAX6 mRNA expression further (FIG. 11B). This result suggests that 10 days is the optimal duration for incubation with NCM (step D).

Figure 11C:
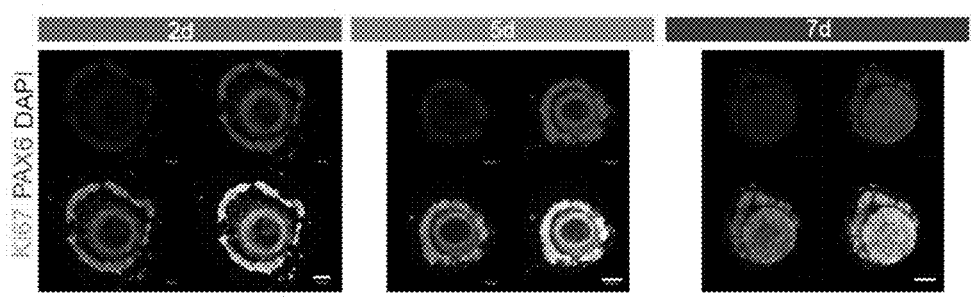
FIG. 11C. Immunofluorescence analysis of PAX6/ki67-positive cells to mark proliferating neuronal progenitor cells.

These experiments also revealed that shortening incubation with NPEM (step E) to 2 or 5 days did not negatively influence PAX6 mRNA expression, compared to the standard of 7 days as in example 2 (FIG. 11A). Further properties of BENOs undergoing NPEM incubation for different amounts of time were studied by immunofluorescence analysis (FIG. 11C). A minimal NPEM incubation of 5 days was found to be preferable because the BENOs displayed robust tissue condensation and neuronal proliferation only after 5 days of NPEM incubation. This result suggests that 5 to 7 days is the optimal duration for incubation with NPEM (step E).

REFERENCES

Birey, Andersen et al., Nature, 2017: "Assembly of functionally integrated human forebrain spheroids."
Chambers, Fasano et al., Nat. Biotechnol., 2009: "Highly efficient neural conversion of human ES and iPS cells by dual inhibition of SMAD signaling."
Crawford and Roelink, Dev. Dyn., 2007: "The notch response inhibitor DAPT enhances neuronal differentiation in embryonic stem cell-derived embryoid bodies independently of sonic hedgehog signaling."
Feng et al., J Med Chem., 2016: "Rho Kinase (ROCK) Inhibitors and Their Therapeutic Potential."
Jucker et al., J Neurosci Res. 1991: "Fetal rat septal cells adhere to and extend processes on basement membrane, laminin, and a synthetic peptide from the laminin A chain sequence."
Kleinman et al., Biochemistry, 1982: "Isolation and characterization of type IV procollagen, laminin, and heparan sulfate proteoglycan from the EHS sarcoma."
Kriks, Shim et al., Nature, 2011: "Dopamine neurons derived from human ES cells efficiently engraft in animal models of Parkinson's disease."
Lancaster et al., Nature, 2013: "Cerebral organoids model human brain development and microcephaly."
Lancaster and Knoblich, Science, 2014: "Organogenesis in a dish: modeling development and disease using organoid technologies."
Qian, Nguyen et al., Cell, 2016: "Brain-Region-Specific Organoids Using Mini-bioreactors for Modeling ZIKV Exposure."
Stover and Schwartz, Methods Mol Biol. 2011: "Adaptation of Human Pluripotent Stem Cells to Feeder-Free Conditions in Chemically Defined Medium with Enzymatic Single-Cell Passaging."
Olsauskas-Kuprys et al., OncoTargets and Therapy, 2013: "Gamma secretase inhibitors of Notch signaling."
Tiburcy et al., Circulation, 2017: "Defined Engineered Human Myocardium with Advanced Maturation for Applications in Heart Failure Modeling and Repair."

The invention claimed is:
1. A method for producing a bioengineered neuronal organoid (BENO) from pluripotent stem cells (PSCs), the method comprising:
(A) providing a source of PSCs;
(B) culturing the PSCs of step (A), wherein the PSCs are embedded in a matrix immersed in serum-free medium;
(C) culturing the PSCs in said matrix of step (B) in serum-free cell culture medium comprising a Rho-associated kinase inhibitor (ROCKi) and fibroblast growth factor-2 (FGF-2);
(D) culturing the forming BENO originating from the PSCs and the matrix of step (C) in serum free cell culture medium comprising retinoic acid and one or more inhibitors of Mothers against decapentaplegic homologue (SMAD) signaling to induce neurogenesis;
(E) culturing the forming BENO of step (D) in serum free cell culture medium comprising transforming growth factor-beta (TGF-beta) and FGF-2 to enhance genesis of stromal cells and neurogenesis; and
(F) culturing the forming BENO of step (E) in serum free cell culture medium comprising TGF-beta and one or more inhibitors of notch signaling to enhance genesis of stromal cells and neurodifferentiation, wherein the matrix comprises collagen, and
wherein the BENO is produced within a three-dimensional (3D) environment, wherein the 3D environment is initially defined by the matrix.

2. The method of claim 1, wherein the matrix does not comprise a composition derived from Engelbreth-Holm-Swarm mouse sarcomas.

3. The method of claim 1, wherein the matrix does not comprise a composition derived from Engelbreth-Holm-Swarm mouse sarcomas or other components of natural origin having a non-defined composition.

4. The method of claim 1, wherein the matrix comprises type I collagen.

5. The method of claim 1, wherein the stromal cells comprise glial cells.

6. The method of claim 1, wherein the medium of step (D) comprises at least two inhibitors of SMAD signaling.

7. The method of claim 1, wherein the inhibitor of the notch signaling of step (F) is N-[(3,5-Difluorophenyl)acetyl]-L-alanyl-2-phenylklycine-1,1-dimethylethyl ester (DAPT).

8. The method of claim 1, wherein the PSCs are human PSCs.

9. The method of claim 1,
wherein step (A) and step (B) are performed on day −1,
wherein step (C) is performed from day −1 to day 0,
wherein step (D) is performed from day 0 to day 10,
wherein step (E) is performed from day 10 to day 15, and
wherein step (F) is performed from day 15 to at least day 28.

10. The method of claim 6, wherein the inhibitors of SMAD signaling comprise noggin and SB 431542.

* * * * *